US009598215B2

United States Patent
Araki et al.

(10) Patent No.: US 9,598,215 B2
(45) Date of Patent: Mar. 21, 2017

(54) FLEXIBLE PACKAGE

(71) Applicant: TOPPAN PRINTING CO., LTD., Tokyo (JP)

(72) Inventors: Jun Araki, Tokyo (JP); Motoo Yanagiuchi, Tokyo (JP); Noriyuki Sasaki, Tokyo (JP); Shunsuke Yajima, Tokyo (JP); Masashi Goto, Tokyo (JP)

(73) Assignee: Toppan Printing Co., Ltd., Tokyo (JP)

( * ) Notice: Subject to any disclaimer, the term of this patent is extended or adjusted under 35 U.S.C. 154(b) by 0 days.

(21) Appl. No.: 14/954,878

(22) Filed: Nov. 30, 2015

(65) Prior Publication Data

US 2016/0083165 A1    Mar. 24, 2016

Related U.S. Application Data

(63) Continuation of application No. 14/803,943, filed on Jul. 20, 2015, which is a continuation of application No. PCT/JP2014/000351, filed on Jan. 24, 2014.

(30) Foreign Application Priority Data

Jan. 25, 2013  (JP) ................................ 2013-012073
Jun. 28, 2013  (JP) ................................ 2013-136467
(Continued)

(51) Int. Cl.
    *B65D 75/58* (2006.01)
    *B65D 75/30* (2006.01)
(Continued)

(52) U.S. Cl.
    CPC .......... *B65D 75/5883* (2013.01); *B31B 29/60* (2013.01); *B31B 29/84* (2013.01);
(Continued)

(58) Field of Classification Search
    CPC B65D 75/5883; B65D 75/5827; B65D 75/30; B65D 75/52; B65D 75/5822; B65D 75/008; B65D 65/38
(Continued)

(56) References Cited

U.S. PATENT DOCUMENTS 4,898,280 A * 2/1990 Runge .................... B29C 65/18
    383/200
5,137,154 A * 8/1992 Cohen .................... B65D 33/02
    206/522
(Continued)

FOREIGN PATENT DOCUMENTS

ES   WO 2005063589 A1 * 7/2005 ............. B65D 33/02
JP   60-15641   2/1985
(Continued)

OTHER PUBLICATIONS

International Search Report issued Apr. 28, 2014 in PCT/JP2014/000351, filed Jan. 24, 2014.
(Continued)

*Primary Examiner* — Donnell Long
(74) *Attorney, Agent, or Firm* — Oblon, McClelland, Maier & Neustadt, L.L.P.

(57) ABSTRACT

A flexible package including a package body including a first side-surface film and a second side-surface film sealed in a peripheral portion. The package body has sealed portions formed in side edge portions such that a non-sealed portion is formed in at least one of the sealed portions. The non-sealed portion has a gas injection portion containing a gas which has a specific heat at constant volume of 0.67 kJ/kg·deg or higher at 0° C. and 1 atm. The gas injection portion has a diameter of from 3 to 50 mm and is formed such that a repelling force is from 4 to 30 N at 23° C. and 1 atm when an entire gas injection portion is nipped from both sides of the first and second side-surface films and
(Continued)

squeezed until a nipped gas injection portion has a width equal to a half of the diameter of the gas injection portion.

18 Claims, 18 Drawing Sheets

(30) Foreign Application Priority Data

| | | |
|---|---|---|
| Jun. 28, 2013 | (JP) | 2013-136468 |
| Jun. 28, 2013 | (JP) | 2013-136469 |
| Jun. 28, 2013 | (JP) | 2013-136470 |
| Jun. 28, 2013 | (JP) | 2013-136471 |
| Aug. 22, 2013 | (JP) | 2013-172171 |

(51) Int. Cl.

| | |
|---|---|
| *B65D 65/38* | (2006.01) |
| *B65D 75/00* | (2006.01) |
| *B65D 75/52* | (2006.01) |
| *B65D 33/02* | (2006.01) |
| *B31B 29/60* | (2006.01) |
| *B31B 29/84* | (2006.01) |
| *G01N 7/00* | (2006.01) |

(52) U.S. Cl.
CPC ............ *B65D 33/02* (2013.01); *B65D 65/38* (2013.01); *B65D 75/008* (2013.01); *B65D 75/30* (2013.01); *B65D 75/52* (2013.01); *B65D 75/5827* (2013.01); *G01N 7/00* (2013.01); *B31B 2219/603* (2013.01); *B31B 2219/9054* (2013.01)

(58) Field of Classification Search
USPC ............... 222/541.6, 105, 566, 107; 206/484
See application file for complete search history.

(56) References Cited

U.S. PATENT DOCUMENTS

| | | | | |
|---|---|---|---|---|
| 5,352,043 | A * | 10/1994 | Takagaki | B31B 1/00 383/104 |
| 5,353,459 | A | 10/1994 | Potter | |
| 5,791,485 | A * | 8/1998 | Carbonneau | B65D 31/02 206/204 |
| 7,585,528 | B2 * | 9/2009 | Ferri | B65D 81/052 206/522 |
| 2002/0000393 | A1 * | 1/2002 | Meyer | B31B 19/98 206/554 |
| 2002/0031703 | A1 * | 3/2002 | Kameyama | H01M 2/0212 429/162 |
| 2004/0035865 | A1 | 2/2004 | Rosen | |
| 2005/0227028 | A1 * | 10/2005 | Shiokawa | B32B 27/08 428/35.2 |
| 2005/0236427 | A1 | 10/2005 | Farha | |
| 2005/0238765 | A1 * | 10/2005 | Weaver | B32B 27/32 426/106 |
| 2005/0255200 | A1 | 11/2005 | Takahagi et al. | |
| 2006/0023976 | A1 | 2/2006 | Alvater et al. | |
| 2006/0266728 | A1 * | 11/2006 | Wilkes | B65D 75/5883 215/381 |
| 2007/0017844 | A1 | 1/2007 | Komatsu et al. | |
| 2007/0089377 | A1 | 4/2007 | Yasuhira | |
| 2007/0158227 | A1 * | 7/2007 | Amano | A61J 1/00 206/438 |
| 2007/0242905 | A1 * | 10/2007 | Weaver | B65D 75/008 383/109 |
| 2012/0125947 | A1 | 5/2012 | Becker et al. | |

FOREIGN PATENT DOCUMENTS

| | | |
|---|---|---|
| JP | 3-17044 U | 2/1991 |
| JP | 7-80986 A | 3/1995 |
| JP | 07-251873 A | 10/1995 |
| JP | 7-251873 A | 10/1995 |
| JP | 8-119294 | 5/1996 |
| JP | 09-254997 | 9/1997 |
| JP | 11-20102 A | 1/1999 |
| JP | 11-54362 | 2/1999 |
| JP | 3073049 U | 11/2000 |
| JP | 2001-240085 | 9/2001 |
| JP | 2001-270533 | 10/2001 |
| JP | 2002-019795 | 1/2002 |
| JP | 2004-520240 | 7/2004 |
| JP | 2004-256126 | 9/2004 |
| JP | 2005-193954 | 7/2005 |
| JP | 1254567 | 10/2005 |
| JP | 2006-027646 | 2/2006 |
| JP | 2006-036213 | 2/2006 |
| JP | 2006-044714 | 2/2006 |
| JP | 2006-44796 A | 2/2006 |
| JP | 2006-123931 | 5/2006 |
| JP | 2006-176207 A | 7/2006 |
| JP | 2006-347566 | 12/2006 |
| JP | 2007-118961 | 5/2007 |
| JP | 3137430 U | 11/2007 |
| JP | 2009-012800 | 1/2009 |
| JP | 2009-184690 | 8/2009 |
| JP | 2011-057237 | 3/2011 |
| JP | 2012-025394 | 2/2012 |
| JP | 2013-136403 A | 7/2013 |
| JP | 2013-141784 A | 7/2013 |
| WO | WO 2005/063589 | 7/2005 |
| WO | WO 2012/071391 A | 5/2012 |

OTHER PUBLICATIONS

Written Opinion of the International Searching Authority mailed Apr. 28, 2014 in connection with PCT/JP2014/000351, filed Jan. 24, 2014.

Office Action issued Mar. 29, 2016 in Japanese Patent Application No. 2013-172171 (with partial English Translation).

* cited by examiner

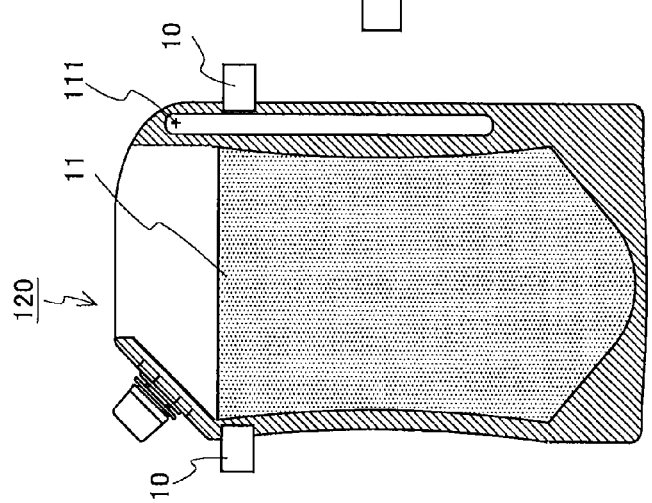

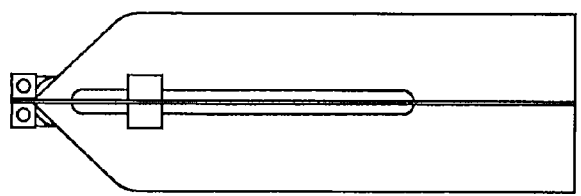
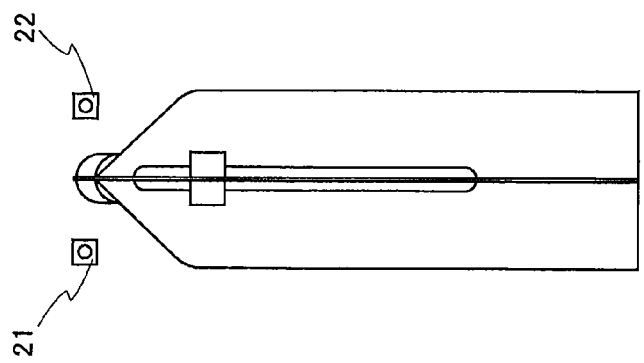
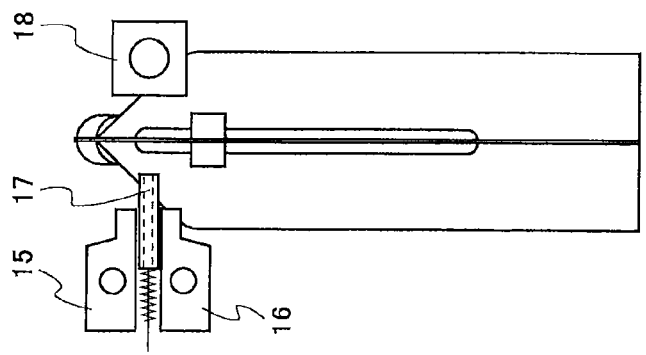

F I G. 9
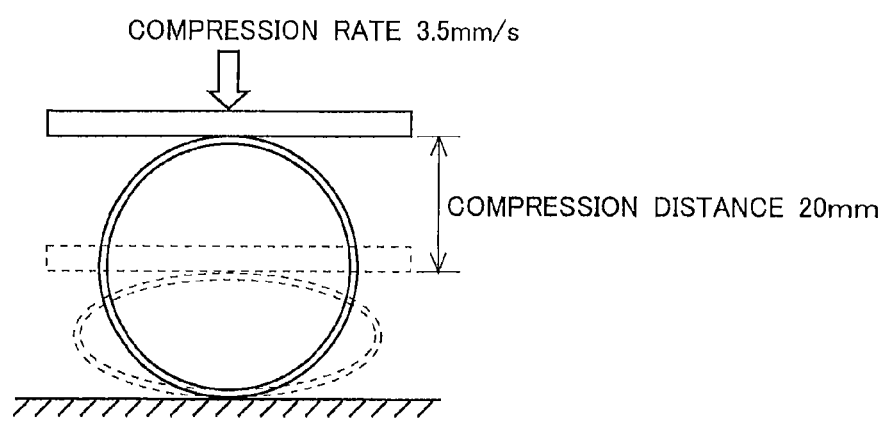

F I G. 1 8
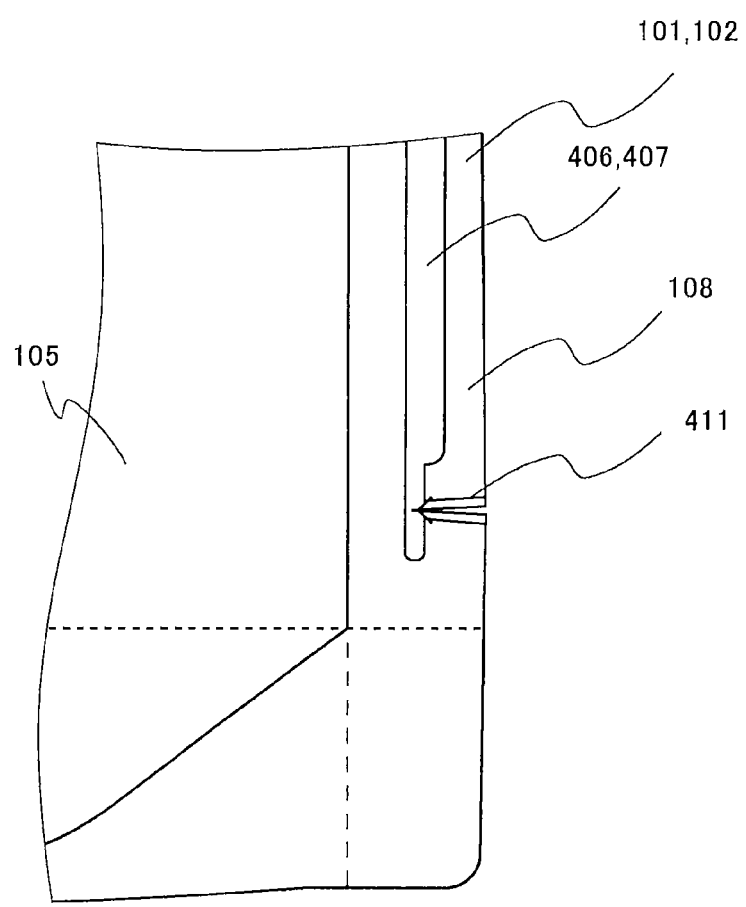

FLEXIBLE PACKAGE

CROSS-REFERENCE TO RELATED APPLICATIONS

The present application is a continuation of Ser. No. 14/803,943, filed Jul. 20, 2015, which is a continuation of International Application No. PCT/JP2014/000351, filed Jan. 24, 2014, which is based upon and claims the benefits of priority to Japanese Application No. 2013-012073, filed Jan. 25, 2013, Japanese Application No. 2013-136467, filed Jun. 28, 2013, Japanese Application No. 2013-136468, filed Jun. 28, 2013, Japanese Application No. 2013-136469, filed Jun. 28, 2013, Japanese Application No. 2013-136470, filed Jun. 28, 2013, Japanese Application No. 2013-136471, filed Jun. 28, 2013, and Japanese Application No. 2013-172171, filed Aug. 22, 2013. The entire contents of all of the above applications are incorporated herein by reference.

BACKGROUND OF THE INVENTION

Field of the Invention

The present invention relates to a flexible package.

Discussion of the Background

As a package for packaging contents such as liquid, a viscous substance, powder, a solid, or the like, a flexible package formed by joining films together and sealing peripheral portions of the films has been known.

As disclosed in Japanese Laid-Open Patent Publications No. 8-119294 and No. 2004-256126, a flexible package is, for example, a pouch whose self-standing property is improved by devising the shape of a bottom surface or the shapes of a bottom surface and a side surface. A bottom gusset type pouch is widely used which is produced by inserting, at a bottom portion of a laminated film (barrel member) having both front and rear surfaces, another laminated film (bottom member) that is folded, and heat-sealing both side edge portions and a bottom edge portion. A flexible package filled with contents and having a sealed opening can be displayed or used on a table, and therefore, is widely used as a resource-saving package substituting for a rigid container.

SUMMARY OF THE INVENTION

According to one aspect of the present invention, a flexible package including a package body including a first side-surface film and a second side-surface film sealed in a peripheral portion such that a storage portion is formed in the package body. The package body has sealed portions formed in side edge portions such that a non-sealed potion is formed in at least one of the sealed portions. The non-sealed portion has a gas injection portion containing a gas which has a specific heat at constant volume of 0.67 kJ/kg·deg or higher at 0° C. and 1 atm. The gas injection portion has a diameter in a range of from 3 mm to 50 mm and is formed such that a repelling force is in a range of from 4 N to 30 N at 23° C. and 1 atm when an entire gas injection portion is nipped from both sides of the first and second side-surface films and squeezed until a nipped gas injection portion has a width equal to a half of the diameter of the gas injection portion.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 4(a)-4(c) are schematic diagrams illustrating a method of filling the flexible package with gas.

FIGS. 6(a)-6(c) are schematic diagrams illustrating a method of filling the flexible package with gas.

FIG. 9 is a schematic diagram illustrating a method of measuring loop stiffness.

FIG. 18 is a partially enlarged view of the flexible package.

DESCRIPTION OF THE EMBODIMENTS

Figure 1:
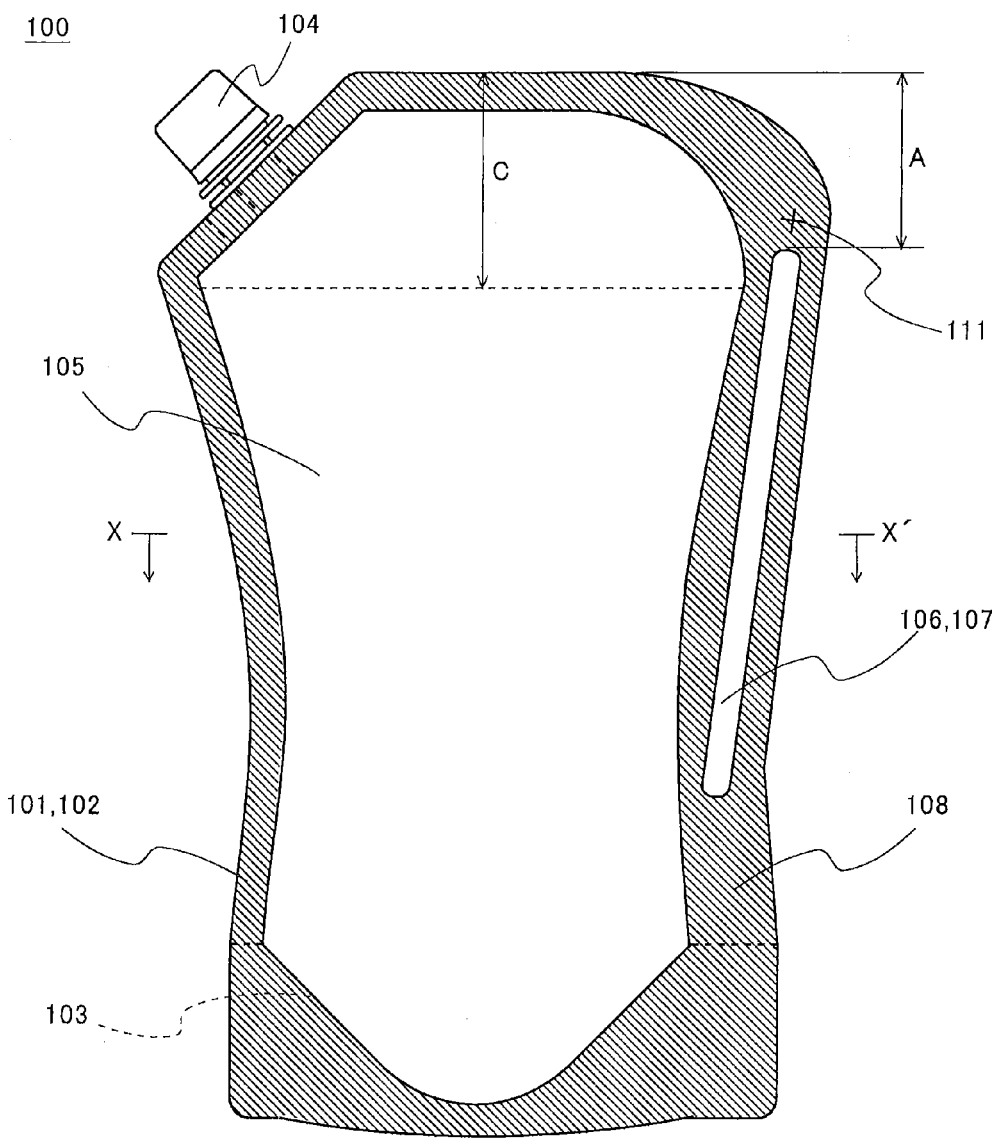
FIG. 1 is a plan view of a flexible package.

The embodiments will now be described with reference to the accompanying drawings, wherein like reference numerals designate corresponding or identical elements throughout the various drawings.

(Summary of Flexible Package)

FIG. 1 is a plan view of a flexible package 100 according to an embodiment. The flexible package 100 is formed by joining a first side-surface film 101, a second side-surface film 102, and a bottom film 103 together. The bottom film 103 is inserted, with a predetermined insertion length, between the first and second side-surface films 101 and 102 such that it is folded in half and inserted from the hold line side. Peripheral portions of these films joined together, excluding a portion through which contents are to be injected, are sealed, thereby forming a storage part 105. Assuming that an end portion of the flexible package 100, from which the bottom film 103 is inserted, faces a downward direction, the portion through which the contents are to be injected is, for example, upper ends of the first side-surface film 101 and the second side-surface film 102.

As a material of the first side-surface film 101, the second side-surface film 102, and the bottom film 103, which form the flexible package 100, for example, a laminate containing resin or aluminum, including a sealant layer at an innermost surface, and having a certain rigidity may be used. As an example of the laminate, there is a laminate having a layer structure of polyethylene terephthalate/aluminum/nylon/low-density polyethylene in a direction from the outer side to the inner side of the flexible package 100.

An end portion in the left-right direction, of the region where the peripheral portions of the first side-surface film 101 and the second side-surface film 102 are sealed, is referred to as a side edge portion 108. In the side edge portion 108, a non-sealed region 106 is provided. The non-sealed region 106 is a region which is not sealed over a predetermined length in the top-bottom direction and is surrounded by the sealed region. The non-sealed region 106 may be provided in either or both of the left and right side edge portions 108.

The flexible package 100 includes a discharge part 104 which is to be opened for discharging the contents. For example, as shown in FIG. 1, the discharge part 104 is formed by attaching a spout member between the first side-surface film 101 and the second side-surface film 102. The shape and structure of the discharge part 104 are not limited thereto, and the discharge part 104 may be omitted.

Figure 2:
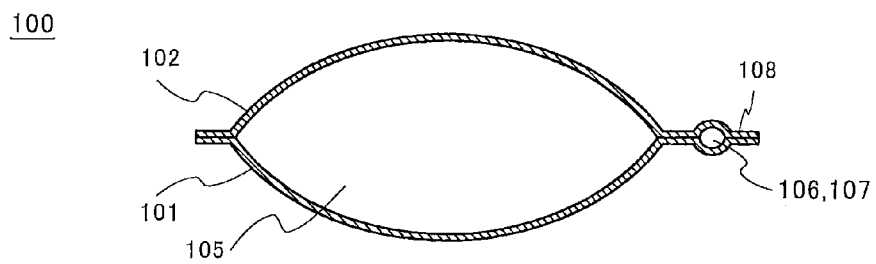
FIG. 2 is a cross-sectional view of the flexible package.

The storage part 105 is, after the contents have been injected therein, is sealed by sealing the upper ends of the first side-surface film 101 and the second side-surface film 102. When the bottom film 103 is expanded so that the first side-surface film 101 and the second side-surface film 102 form a cylindrical shape on the side where the bottom film 103 is sealed, the flexible package 100 is allowed to stand by itself with the bottom film 103 being a bottom surface. FIG. 1 is a plan view of the flexible package 100 in this state, and FIG. 2 is a cross-sectional view taken along a X-X' line in FIG. 1.

In the non-sealed region 106, gas is injected through a slit 111 to expand the first side-surface film 101 and the second side-surface film 102, thereby forming a gas injection portion 107. In a region where the slit 111 is formed, after the formation of the gas injection portion 107, the first side-surface film 101 and the second side-surface film 102 are sealed to prevent the gas from escaping through the slit 111. If the slit 111 is positioned near an upper end of the non-sealed region 106, the sealing to seal the storage part 105 and the sealing to seal the portion near the slit 111 can be performed in the same process step. A production method for the flexible package 100 will be described later in detail.

As described above, since the gas injection portion 107 is provided in the side edge portion 108 of the flexible package 100, the first side-surface film 101 and the second side-surface film 102 are less likely to bend at the gas injection portion 107 and its vicinity. Therefore, when the flexible package 100 is made to stand by itself, the overall shape of the flexible package 100 is less likely to deform, and thus the self-standing property thereof is easily maintained. When the flexible package 100 is carried or when the contents are taken out, the first side-surface film 101 and the second side-surface film 102 around the gas injection portion 107 serve as a handle. Therefore, a user can easily hold the flexible package 100 by grasping the gas injection portion 107. In the flexible package 100 according to the present embodiment, excellent shape retaining property provided by the gas injection portion 107 can stabilize the position of the outlet when the contents, even if the amount of the contents is small, are taken out of the package 100, and thus discharge of the contents is facilitated. When the flexible package 100 having the contents therein is heated in hot water or a microwave oven, the storage part 105 of the flexible package 100 becomes hot due to the heated contents. However, the user, holding the gas injection portion 107, can hold the flexible package 100 without feeling hot.

(Production Method for Flexible Package)

Hereinafter, a production method for the flexible package 100 will be described.

First, the first side-surface film 101 and the second side-surface film 102, each having a sealant layer, are disposed so that the sealant layers thereof oppose each other. The bottom film 103 having a sealant layer is folded in half so that the sealant layer faces outside, and the folded bottom film 103 is inserted between the first side-surface film 101 and the second side-surface film 102 so that a fold line faces inside the first side-surface film 101 and the second side-surface film 102.

Next, the peripheral portions of the first side-surface film 101 and the second side-surface film 102 are heat-sealed, excluding the non-sealed region 106, a region where the discharge part 104 is to be attached, and a region to be an opening for injection of contents. Thereby, in the portion where the bottom film 103 is inserted, the first side-surface film 101 and the bottom film 103 are sealed together, and the second side-surface film 102 and the bottom film 103 are sealed together. In the portion where the bottom film 103 is not inserted, the first side-surface film 101 and the second side-surface film 102 are sealed together, excluding the regions not to be sealed (i.e., the region to be the non-sealed region 106, the region where the discharge part 104 is to be attached, and the region to be an opening for injection of contents). In a region near the upper end of the non-sealed region 106, simultaneously with the heat sealing or at a time before or after the heat sealing, the slit 111 for gas injection is formed in one or both of the first side-surface film 101 and the second side-surface film 102. Further, simultaneously with the heat sealing or at a time before or after the heat sealing, the peripheral portions of the first side-surface film 101, the second side-surface film 102, and the bottom film 103 are cut, thereby to form these films in a desired plane shape.

Next, in the region where the discharge part 104 is to be attached, the discharge part 104, which is separately formed, is inserted between the first side-surface film 101 and the second side-surface film 102, and overlapping portions of the first side-surface film 101, the second side-surface film 102, and the discharge part 104 are heat-sealed. The attachment of the discharge part 104 may be performed simultaneously with the heat sealing of the first side-surface film 101, the second side-surface film 102, and the bottom film 103. Through the above-described process steps, a blank 120 shown in FIG. 3 is produced.

(Gas Filling Method)

Figure 3:
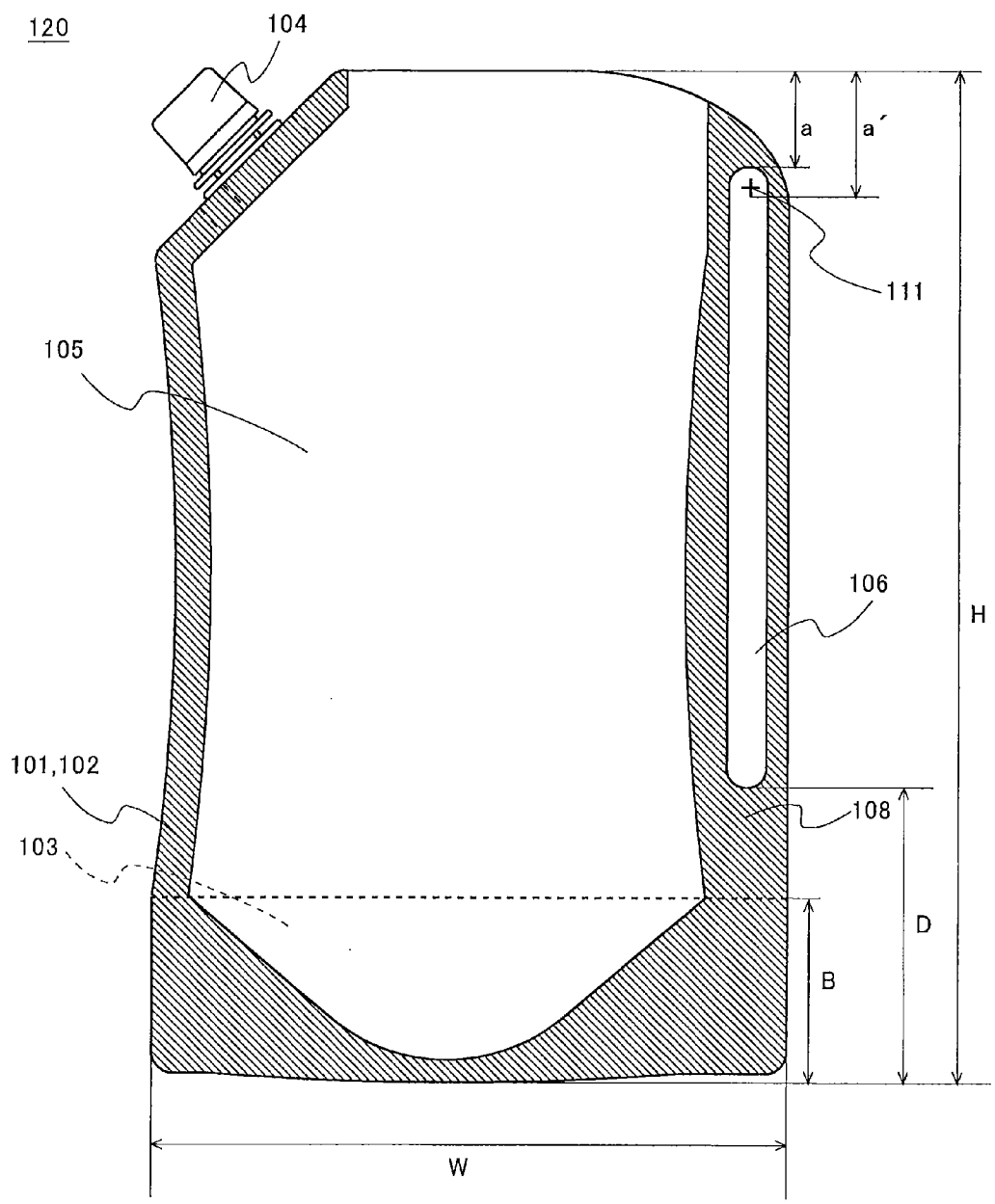
FIG. 3 is a plan view of a blank of the flexible package.

FIG. 4(a) to FIG. 6(c) are diagrams illustrating a method of filling gas in the non-sealed region 106 of the blank 120 shown in FIG. 3, simultaneously with the process step of filling contents in the blank 120 and sealing the opening portion. The blank 120 is held at the both side edge portions 108 thereof by a gripper of a well-known intermittent rotation type rotary pouch packaging device, is hung, and is intermittently transferred. At stop positions, the packaging steps such as opening of the blank 120, filling of contents, sealing of the opening portion, and the like are sequentially performed.

As shown in FIG. 4(a), the blank 120 held by the gripper 10 is filled with contents 11 at a contents filling position, and subsequently, is rotationally moved and stopped at a gas filling position (FIG. 4(b)), where a gas filling step is performed. In the gas filling step, a tip of a later-described gas blowing nozzle 17 is applied to the slit 111, and gas is blown through the slit 111 into the non-sealed region 106. Subsequently, a portion directly beneath the slit 111 is heat-sealed (seal portion 12), whereby the non-sealed region 106 is hermetically sealed to enclose the pressurized gas therein. Thereby, the non-sealed region 106 (gas injection portion 107) in which the pressurized gas is enclosed is formed in the side edge portion 108 of the blank 120. In the gas filling step, simultaneously with the heat sealing directly beneath the slit 111, the upper end of the blank 120 is linearly sealed to form a line seal portion 13. Subsequently, the blank 120 is rotationally moved and stopped at a sealing position (FIG. 4(c)), where a sealing step is performed. In this sealing step, the opening including the slit 111 is flatly sealed to form a seal portion 14. At this time, the portion of the slit 111 may be fused to improve the appearance.

Figure 5C:
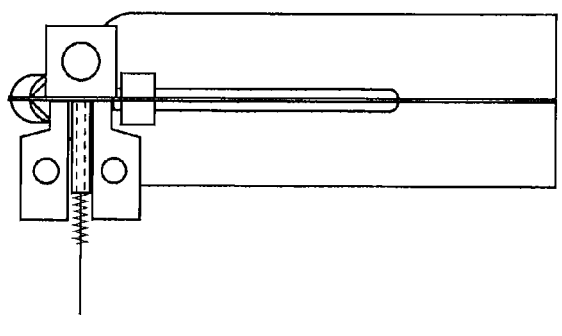
FIGS. 5(a)-5(c) are schematic diagrams illustrating a method of filling the flexible package with gas.
Figure 5B:
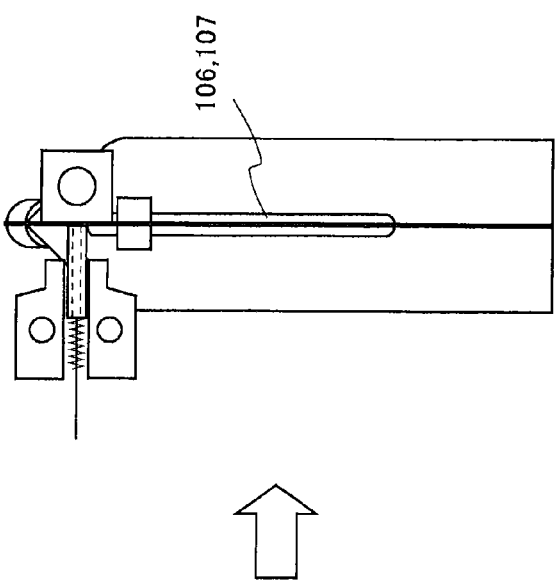
Figure 5A:
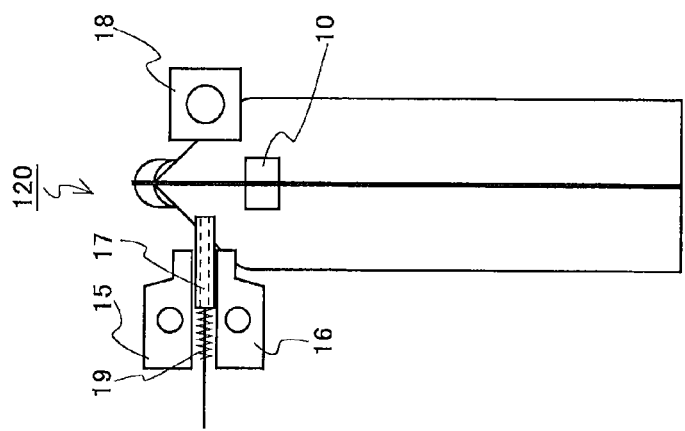

While in this example, the slit 111 is formed in the non-sealed region 106 as the gas blowing part, a hole may be formed instead of the slit 111. However, when a hole is formed, the fused films may adhere to a heating plate for sealing or overflow through the hole. Therefore, it is preferable to form a slit like the slit 111 that prevents the above drawbacks. Further, in this example, the slit 111 is formed near the upper end of the non-sealed region 106, but the position of the slit 111 is not particularly limited. However, when the slit 111 is formed near the upper end, gas sealing can be performed by sealing a portion directly beneath the slit 111. In addition, as shown in FIGS. 5(a)-5(c) described later, sealing of the non-sealed region 106 can be performed simultaneously with line sealing which is usually performed, and a receiving member (heating plate) for the line sealing can be used. Therefore, the slit 111 is desirably formed near the upper end. Further, in this example, the sealing of the opening portion is performed in each of the gas filling step and the sealing step (two times in total). However, sealing may be performed only in the sealing step while omitting the sealing in the gas filling step, or sealing may be performed only in the gas filling step while omitting the sealing step.

Next, the respective steps shown in FIGS. 4(a)-4(c) will be described in more detail with reference to FIGS. 5(a)-5(c), 6(a)-6(c) and 7. FIGS. 5(a), 5(b) and 5(c) and FIG. 6(a) sequentially show the gas filling step performed on the blank 120 (already filled with contents) stopped at the gas filling position, and the sealing step performed on the blank 120 stopped at the sealing position. In the gas filling position, a heating plate 15 for line sealing of the opening, a heating plate 16 for sealing of the non-sealed region 106, and a gas blowing nozzle 17 at an intermediate height between them are disposed on one side, and a heating plate 18 as a receiving member is disposed on the other side across the blank 120. The heating plates 15 and 16 and the gas blowing nozzle 17 are simultaneously movable forward and backward. The gas blowing nozzle 17 is urged forward by a spring 19, and slightly protrudes forward relative to the heating plates 15 and 16.

Figure 7:
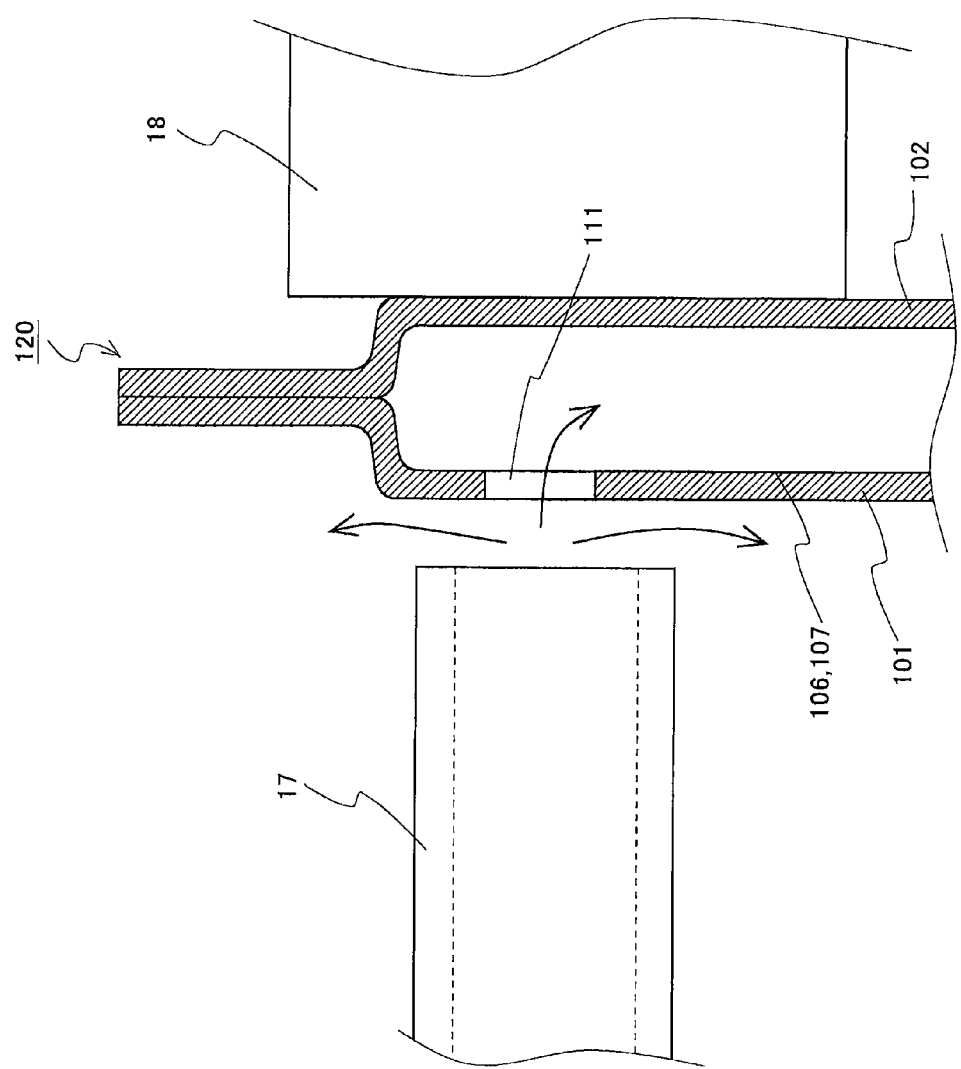
FIG. 7 is an enlarged schematic diagram illustrating a method of filling the flexible package with gas.

When the blank 120 stops at the gas filling position (FIG. 5(a)), the heating plates 15 and 16 and the gas blowing nozzle 17 move forward as shown in FIG. 5(b), and the cylindrical tip of the gas blowing nozzle 17 comes into contact with the periphery of the slit 111 formed in the non-sealed region 106. Meanwhile, on the back surface side, the heating plate 18 moves forward and supports the back surface side of the blank 120 (back surface side of the slit 111), and simultaneously, gas is blown out from the gas blowing nozzle 17. When the gas blowing starts, the gas pressure causes the gas blowing nozzle 17 to slightly move backward against the urging force as shown in FIG. 7, and a gap is formed between the first side-surface film and the second side-surface film. Then, the gas is blown into the non-sealed region 106 through the slit 111, and thereby the non-sealed region 106 expands. When the urging force is F, the gas pressure is P, and the nozzle opening area is S, the relationship between the urging force and the gas pressure is set to $F < P \times S$. In the state where the blank 120 is closely sandwiched between the gas blowing nozzle 17 and the heating plate 18 and the first side-surface film and the second side-surface film are closely adhered to each other at the entire periphery of the slit 111, gas blowing is not performed. A gap needs to be formed between the first side-surface film and the second side-surface film at the entirety or part of the periphery of the slit 111.

Subsequently, as shown in FIG. 5(c), the heating plates 15 and 16 further move forward, and the heating plate 15 comes into contact with the upper end of the opening of the blank 120 while the heating plate 16 comes into contact with a position directly beneath the slit in the non-sealed region 106, whereby the line seal portion 13 and the seal portion 12 are formed, and simultaneously, gas blowing from the gas blowing nozzle 17 stops. Subsequently, as shown in FIG. 6(a), the heating plates 15 and 16, the gas blowing nozzle 17, and the heating plate 18 move backward. Meanwhile, the blank 120 is rotationally moved to the following sealing position (FIG. 6(b)). In the sealing position, a pair of heating plates 21 and 22 are disposed facing each other across the blank 120. When the blank 120 stops at this position, as shown in FIG. 6(c), the heating plates 21 and 22 move forward and flatly seals the opening including the slit 111, whereby a seal portion 14 is formed. After the formation of the seal portion 14, the blank 120 is rotationally moved, and the opening is cooled and sealed at the following cooling position (not shown). Further, the gripper is opened at a release position to release the blank 120. Through the above-described process steps, the gas is filled in the non-sealed region 106, whereby the gas injection portion 107 is formed.

(Gas Injected to Gas Injection Portion)

The gas to be injected into the gas injection portion 107 to form the non-sealed region 106 is not limited. For example, a gas having specific heat at constant volume equal to or larger than 0.67 kJ/kg·deg at 0° C. and 1 atm (101.325 kPa) may be used. When such a gas is used, even if the temperature of the contents or the outside air temperature is high, the temperature of the inside of the gas injection portion 107 is not likely to rise, whereby pressure increase can be suppressed. Thus, it is possible to reduce the possibility of peeling from near the gas injection portion 107 to the side edge of the flexible package 100, and leakage of the gas to the outside from a gap between the first side-surface film 101 and the second side-surface film 102.

(Repelling Force of Gas Injection Portion)

Figure 8A:
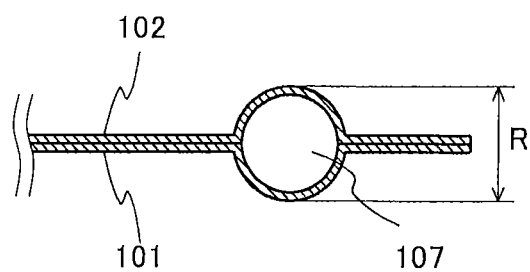
FIGS. 8(a) and 8(b) are cross-sectional views of a gas injection portion of the flexible package.
Figure 8B:
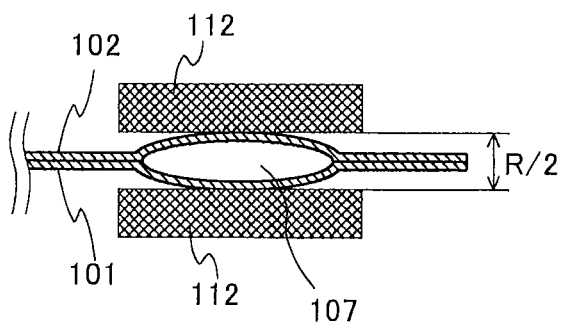

The stability of self-standing of the flexible package 100 and the ease of discharging the contents are increased as the gas injection portion 107 is less likely to bend. The gas injection portion 107 is less likely to bend as the repelling force when the gas injection portion 107 is squeezed is larger. The inventors have discovered that the difficult-to-bend property of the gas injection portion 107 can be favorably evaluated by measuring the repelling force when the entirety of the gas injection portion 107 is nipped from the first side-surface film 101 side and the second side-surface film 102 side and is squeezed until the width of the nipped portion 107 becomes half the diameter R of the gas injection portion 107. FIG. 8(a) shows an enlarged cross-sectional view of the gas injection portion 107 which is not squeezed, and FIG. 8(b) shows an enlarged cross-sectional view of the squeezed gas injection portion 107. As shown in FIGS. 8(a) and 8(b), when the entirety of the gas injection portion 107 is nipped between flat surfaces of two jigs 112 and squeezed up to the width half the diameter R, the volume reduction rate of the gas injection portion 107 can be a constant value that does not depend on the diameter R and the length. The repelling force applied to the jigs 112 at this time may be regarded as a restoring force of the entirety of the gas injection portion 107 to restore to the original shape. Therefore, it is conceivable that, by using the above method, the difficult-to-bend property of the gas injection portion 107 can be evaluated without greatly depending on the size of the gas injection portion 107.

The repelling force is preferably 4 N or more at 23° C. and 1 atm (101.325 kPa) since the stability of the flexible package 100 in its self-standing posture is improved. More preferably, the repelling force is 7 N or more since the shape of the flexible package 100 when the contents are discharged is not deformed and thereby the ease of discharging the contents is improved. If the repelling force is 30 N or less, it is possible to prevent the situation where, at 23° C., the gas injection portion 107 is broken or the seal portion near the gas injection portion 107 is peeled and thereby the gas leaks to the outside. More preferably, the repelling force is 26 N or less since such leakage of the gas can be prevented even if the temperature of the gas injection portion 107 is as high as 50° C. Therefore, the repelling force is, at 23° C. and 1 atm, preferably not smaller than 4 N but not larger than 30 N, and more preferably, not smaller than 4 N but not larger than 26 N. By adjusting the repelling force within this range, it is possible to provide a flexible package including a gas injection portion that has a constant difficult-to-bend property and reduces the possibility of leakage of the gas. Such adjustment of the repelling force can be realized by controlling the pressure of the gas blown into the gas injection portion 107.

(Rigidity of Side-Surface Films)

The flexible package 100 may have the following features. That is, loop stiffness LSv of the first side-surface film 101 and the second side-surface film 102 in a direction corresponding to the top-bottom direction of the self-standing flexible package 100 is not smaller than 30 mN/25 mm (width) but not larger than 1300 mN/25 mm (width), and loop stiffness LSh of the first side-surface film 101 and the second side-surface film 102 in a direction corresponding to the left-right direction of the self-standing flexible package 100 is not smaller than 20 mN/25 mm (width) but not larger than 1200 mN/25 mm (width). The loop stiffness is as follows. That is, as shown in FIG. 9, a loop is formed by using a film cut into a strip shape of a predetermined size, and the loop is pressed by a predetermined amount in the diameter direction, and then the repelling force of the loop is measured. The loop stiffness is the measured repelling force, and is an index indicating the rigidity of the film. The larger the value of the loop stiffness is, the higher the rigidity of the film is. How to measure the loop stiffness will be described later.

If the values of loop stiffnesses LSv and LSh go below the above range, when the flexible package 100 is made to stand by itself, the shape of the flexible package 100 cannot be retained by only the rigidity of the gas injection portion 107, resulting in undesirable situations such as bending of the upper portion of the flexible package 100, and falling of the flexible package 100. On the other hand, if the values of the loop stiffnesses LSv and LSh exceed the above range, the toughness of the first side-surface film 101 and the second side-surface film 102 is excessively increased, which makes the package forming processing difficult.

Within the above range, more preferably, the value of the loop stiffness LSh is not smaller than 80 mN/25 mm (width) but not larger than 550 mN/25 mm (width), and the value of the loop stiffness LSv is not smaller than 80 mN/25 mm (width) but not larger than 480 mN/25 mm (width). In this case, the self-standing property of the flexible package 100 can be stably maintained, and the package forming processing is facilitated.

Within the above range, when the value of the loop stiffness LSh is not smaller than 20 mN/25 mm (width) but not larger than 80 mN/25 mm (width) and the value of the loop stiffness LSv is not smaller than 30 mN/25 mm (width) but not larger than 80 mN/25 mm (width), a thinner and cheaper film can be used as the first side-surface film 101 and the second side-surface film 102 as compared to the case where a flexible package having no gas injection portion 107 is configured. Therefore, in addition to the excellent self-standing property of the flexible package 100 and the easiness of the package forming processing, the production cost of the flexible package 100 can be reduced.

The material of the first side-surface film 101 and the second side-surface film 102 is not particularly limited. For example, a multilayer film including a sealant layer as an innermost layer may be used. The first side-surface film 101 and the second side-surface film 102 may include a resin layer, a metal foil layer, a vapor deposition layer of metal or inorganic oxide, or the like, depending on the purpose of the flexible package 100. The effect of improving the self-standing property of the flexible package 100 and the easiness of processing thereof can be achieved by setting the values of the loop stiffnesses LSv and LSh within the above range, without depending on the layer structure of the first side-surface film 101 and the second side-surface film 102.

Generally, a flow direction (MD: Machine Direction) of the first side-surface film 101 and the second side-surface film 102 corresponds to the left-right direction of the self-standing flexible package 100, and a direction (TD: Transverse Direction) perpendicular to the flow direction of the first side-surface film 101 and the second side-surface film 102 corresponds to the top-bottom direction of the self-standing flexible package 100. Thereby, a long film can be used without waste, and the package forming processing can be performed at a high speed. However, even when the MD of the first side-surface film 101 and the second side-surface film 102 does not correspond to the left-right direction of the self-standing flexible package and the TD of the first side-surface film 101 and the second side-surface film 102 does not correspond to the top-bottom direction of the self-standing flexible package, it is possible to achieve both improvement of the self-standing property of the flexible package 100 and the easiness of the package forming processing, as long as the values of the loop stiffness LSv and the loop stiffness LSh are within the above ranges.

As described above, by combining the gas injection portion 107 provided in the side edge portion 108 of the flexible package 100 with the optimized rigidity (loop stiffness) of the first side-surface film 101 and the second side-surface film 102, the first side-surface film 101 and the second side-surface film 102 are less likely to bend at the gas injection portion 107 and its vicinity. Therefore, when the flexible package 100 is made to stand by itself, the overall shape of the flexible package 100 is also less likely to deform, and thus the self-standing property of the flexible package 100 is easily maintained. Further, since the rigidity of the first side-surface film 101 and the second side-surface film 102 is appropriate, the forming processing of the flexible package 100 is facilitated.

(Gas Barrier Property)

The flexible package 100 may have the following features. That is, the amount of the gas permeating the non-sealed region 106 may be controlled by giving gas barrier property to at least the non-sealed region 106. Specifically, in the flexible package 100 according to the present embodiment, at 20° C. and 60% RH, oxygen permeability of the non-sealed region 106 is not lower than 0 cc/(m²·day·atm) but not higher than 30 cc/(m²·day·atm) [not lower than 0 cm³/(m²·day·MPa) but not higher than 296.08 cm³/(m²·day·MPa)]. By setting the oxygen permeability of the non-sealed region 106 to be not higher than 30 cc/(m²·day·atm) at 20° C. and 60% RH, reduction in the inner pressure of the gas injection portion 107 formed by injecting the gas in the non-sealed region 106 is suppressed. Therefore, the shape retaining property of the flexible package 100 due to the gas injection portion 107 and the function of the gas injection portion 107 as a handle can be maintained for a long period of time. In order to further suppress reduction in the inner pressure of the gas injection portion 107, the oxygen permeability of the non-sealed region 106 is, at 20° C. and 60% RH, preferably not lower than 0 cc/(m²·day·atm) but not higher than 5 cc/(m²·day·atm) [not lower than 0 cm³/(m²·day·MPa) but not higher than 49.34 cm³/(m²·day·MPa)], and more preferably, not lower than 0 cc/(m²·day·atm) but not higher than 1 cc/(m²·day·atm) [not lower than 0 cm³/(m²·day·MPa) but not higher than 9.86 cm³/(m²·day·MPa)].

As described above, any type of gas may be adopted as the gas injected into the non-sealed region 106. However, since oxygen permeability is usually adopted as an index indicating the gas barrier property of a film, oxygen permeability may be adopted as a value representing the gas barrier property of the non-sealed region 106. By using a film whose oxygen permeability value is within the above range, reduction in the inner pressure of the gas injection portion 107 can be suppressed regardless of the type of the gas to be sealed, whereby the shape retaining property of the flexible package 100 and the function of the flexible package 100 as a handle can be maintained.

As a method of giving gas barrier property to the non-sealed region 106, a multilayer film including a gas barrier layer made of a material having gas barrier property may be used as the first side-surface film 101 and the second side-surface film 102. Alternatively, a gas barrier layer may be partially provided in a region where the non-sealed region 106 is provided. Examples of the gas barrier layer include: a metal foil such as aluminum, a metal deposition layer such as aluminum, an inorganic oxide deposition layer, a resin film composed of a resin having high gas barrier property, such as nylon, a gas barrier film obtained by depositing metal or inorganic oxide on the surface of a resin film, and a barrier coat layer formed by coating of a barrier coating agent. Examples of the inorganic oxide deposition layer include deposition films of silicon oxide, aluminum oxide, magnesium oxide, titanium oxide, tin oxide, and the like.

As a method of partially giving gas barrier property to the non-sealed region 106, metal or inorganic oxide may be partially deposited on a portion, including a region to be the non-sealed region 106, of the first side-surface film 101 and the second side-surface film 102. Alternatively, the portion including the region to be the non-sealed region 106 may be partially coated with a barrier coating agent. Alternatively, a film including a gas barrier layer may be partially bonded to the portion including the region to be the non-sealed region 106. When gas barrier property is not necessary for the contents filled in the flexible package 100, the method of coating the barrier coating agent is preferable because, in this method, gas barrier property can be partially given easily and inexpensively.

As the above-described gas barrier film, a film having the following structure may be used.

Figure 10:
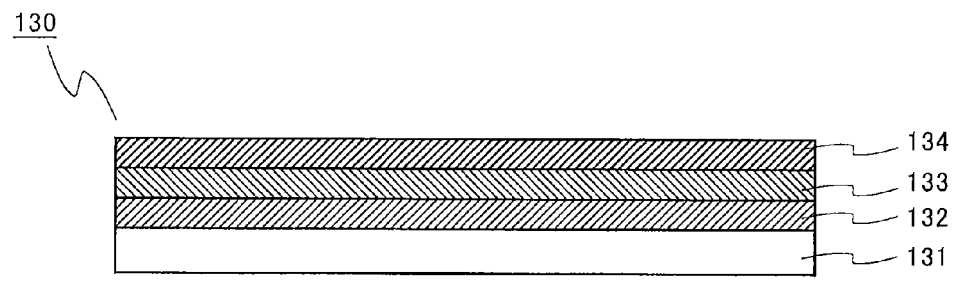
FIG. 10 is a schematic cross-sectional view of a laminated structure of a gas barrier film.

FIG. 10 is a schematic cross-sectional view showing an example of a layer structure of the gas barrier film.

A gas barrier film 130 shown in FIG. 10 is configured by laminating a base material 131, a foundation layer 132, a vapor-deposited layer 133, and a gas barrier coating layer 134 in this order.

As the base material 131, a stretched nylon film, a stretched polyester film, a stretched polypropylene film, or the like may be used.

The foundation layer 132 is a layer provided for enhancing adhesion of the vapor-deposited layer 133. An example of a method for forming the foundation layer 132 is as follows. First, in a dilute solvent such as ethyl acetate, 1 part by weight of γ-isocyanatopropyltriethoxysilane and 5 parts by weight of acrylic polyol are mixed, and stirred. Next, in this mixed solution, as isocyanate compounds, XDI (xylylene diisocyanate) and IPDI (isophorone diisocyanate) are further mixed. The amount of each isocyanate compound is controlled so that the number of moles of isocyanate group (NCO group) of the isocyanate compound is equal to the number of moles of hydrogen group (OH group) of acrylic polyol. The solution in which the isocyanate compounds are added is diluted so that the total solid content is 2% by weight, and the diluted solution is applied to the surface of the base material 131 by gravure coating, thereby forming the foundation layer 132.

The vapor-deposited layer 133 is a gas barrier layer formed by vapor deposition of an inorganic oxide such as silicon oxide, aluminum oxide, magnesium oxide, titanium oxide, tin oxide or the like.

The gas barrier coating layer 134 is a gas barrier layer formed by coating of a barrier coating agent. An example of a method of forming the gas barrier coating layer 134 is as follows. First, 89.6 g of 0.1 N hydrochloric acid is added to 10.4 g of tetraethoxysilane ($Si(OC_2H_5)_4$), and the resultant solution is stirred for 30 minutes to be hydrolyzed. Next, the hydrolyzed solution having a solid content of 3.0% by weight (a value based on the weight of $SiO_2$), which is obtained by the hydrolysis, is mixed with water-isopropyl alcohol solution (water:isopropyl alcohol (weight ratio)=90:10) containing 3.0% by weight of polyvinyl alcohol, at a ratio of 60:40, thereby preparing a barrier coating agent. The prepared barrier coating agent is coated over the vapor-deposited layer 133, thereby forming the gas barrier coating layer 134.

As described above, in the flexible package 100 having the gas injection portion 107, the oxygen permeability of the non-sealed region 106 is set within the above-described range, whereby reduction in the inner pressure of the gas injection portion 107 can be suppressed. As a result, the shape retaining property of the flexible package 100 and the function of the gas injection portion 107 as a handle can be maintained for a long period of time.

(Seal Strength)

The flexible package 100 may have the following features. That is, the seal strength of the side edge portion 108 in which the non-sealed region 106 is formed or the gas injection portion 107 is further formed may be set to 30 N/15 mm or more. Thereby, the seal is not peeled by the gas pressure when the gas injection portion 107 is formed or by increase in the pressure when the temperature inside the formed gas injection portion 107 is high, and thus the possibility of gas leakage or flow of the contents into the gas injection portion is reduced. The side edge portion 108 is a portion in which at least the first side-surface film 101 and the second side-surface film 102 are sealed with each other, and may include or may not include a portion in which the first side-surface film 101 and the bottom film 103 are sealed with each other or a portion in which the second side-surface film 102 and the bottom film 103 are sealed with each other. The seal strength is preferably 50 N/15 mm or higher since the strength of the flexible package 100 can be ensured more sufficiently.

If the seal strength is excessively high, processing costs for sealing, such as the temperature, time, and pressure, are high. In addition, at the boundary between the non-sealed region 106 and the sealed region, the first side-surface film 101 and the second side-surface film 102 may be spuriously adhered to each other, which may deform the shape of the non-sealed region 106 or the gas injection portion 107. The seal strength is more preferably 100 N/15 mm or lower. In this case, the costs of the sealing process are reduced. in addition, since spurious adhesion is suppressed, the non-sealed region 106 or the gas injection portion 107 can be formed without shape deformation.

(Shape)

The flexible package 100 or the blank 120 may have any of the following features.

<Shape of Blank: First Feature>

As shown in FIG. 3, the distance a from the upper end of the non-sealed region 106 to the upper end of the blank 120 is 30% or less of the height H of the blank 120. When a slit such as the slit 111 or a hole is formed at the upper end of the non-sealed region 106, the distance a' from the lower end of the slit or hole to the upper end of the blank 120 is also 30% or less of the height H of the blank 120. When a plurality of non-sealed regions 106 are provided, at least one of the non-sealed regions 106 may satisfy this condition.

<Shape of Blank: Second Feature>

The length W (hereinafter referred to as "width W") in the left-right direction along the first side-surface film 101 or the second side-surface film 102 at the lower end of the blank 120, and the distance B from the lower end of the blank 120 to the fold line of the bottom film 103, i.e., the insertion length B of the bottom film 103, satisfy the relationship of $0.15 \leq (B/W) < 0.5$.

<Shape of Blank: Third Feature>

The lower end of the discharge part 104 of the blank 120 is positioned below the upper end of the non-sealed region 106. When a slit such as the slit 111 or a hole is formed at the upper end of the non-sealed region 106, the lower end of the discharge part 104 is positioned below the lower end of the slit or the hole.

The flexible package 100 in the state where contents are filled in the blank 120 having the above features has the following features.

<Shape of Flexible Package: Fourth Feature>

As shown in FIG. 1, the distance A from the upper end of the gas injection portion 107 to the upper end of the flexible package 100 is 30% or less of the height H of the flexible package 100. The flexible package 100 has this fourth feature when the blank 120 has the above first feature and no slit 111 is formed at the upper end of the non-sealed region 106. When the slit 111 is formed at the upper end of the non-sealed region 106, the flexible package 100 is allowed to have the fourth feature by when an appropriate range near the slit 111 is sealed. When a wider range including a portion lower than the lower end of the slit 111 is sealed in order to prevent, more reliably, the gas from escaping through the slit 111, the slit 111 may be provided at a higher position.

<Shape of Flexible Package: Fifth Feature>

The contents are injected up to a height that does not exceed the upper end of the gas injection portion 107. That is, the distance C from the upper end of the contents to the upper end of the flexible package 100 and the distance A from the upper end of the gas injection portion 107 to the upper end of the flexible package 100 satisfy the relationship of $C \geq A$. The flexible package 100 generally has this fifth feature when the blank 120 has the above third feature, because, generally, the contents are injected into the storage part 105 to a height that does not reach the lower end of the opening of the discharge part 104 so as to prevent the contents from accidentally spilling out from the discharge part 104. Even when the blank 120 does not have the third feature, the flexible package 100 is allowed to have the fifth feature by controlling the amount of the contents to be injected with reference to the height of the upper end of the gas injection portion 107 instead of the height of the discharge part 104. Therefore, the blank 120 may not have the third feature.

When the blank 120 has the second feature, the flexible package 100 also has the second feature, and the width W and the insertion length B satisfy the relationship of $0.15 \leq (B/W) < 0.5$. Thereby, in the flexible package 100, the bottom sides of the first side-surface film 101 and the second side-surface film sufficiently expand, and the bottom film 103 sufficiently stretches. Thus, the flexible package 100 is easily made to stand by itself, and the storage part can be favorably formed. In addition, when the flexible package 100 has the fourth and fifth features, the gas injection portion 107 may be provided up to a position higher than the contents to make the shape of the flexible package 100 difficult to deform. Thus, the flexible package 100 can easily retain the self-standing posture, and the contents can be easily injected. Further, the first feature and the third feature make it easy to obtain the fourth feature and the fifth feature, respectively.

Figure 11:
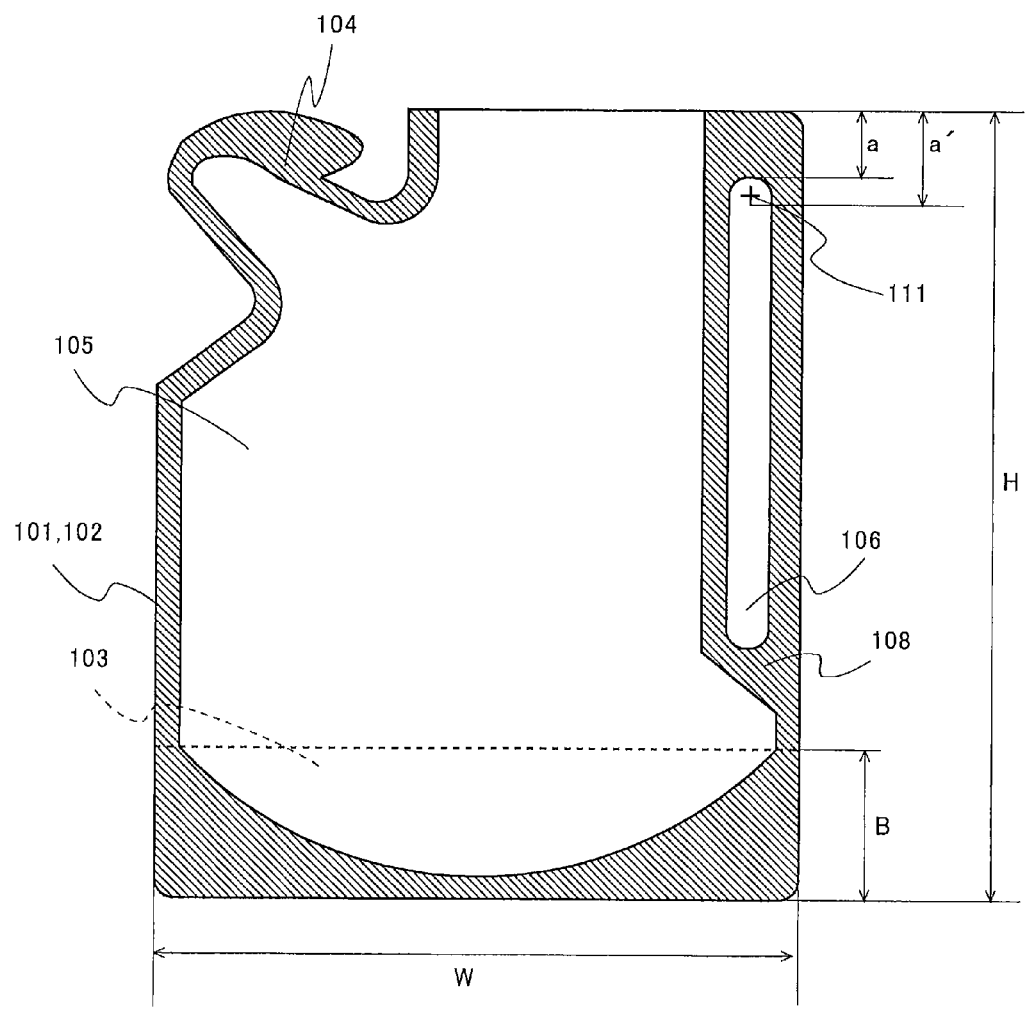
FIG. 11 is a plan view of a flexible package.

FIG. 11 shows a plan view of a blank 200 according to a modification of the blank having the above features. In the blank 200, the discharge part 104 is formed not by attaching a spout member but by molding the first side-surface film 101 and the second side-surface film 102 in a nozzle shape. Thus, the structure of the discharge part 104 of the blank or the flexible package is not particularly limited. For example, the discharge part 104 may be a slit that leads to an opening. The blank and the flexible package need not have all the above-mentioned features. For example, the blank may have only the second feature, and the flexible package may have only the fourth and fifth features.

(Cut Guide Portion)

Figure 12A:
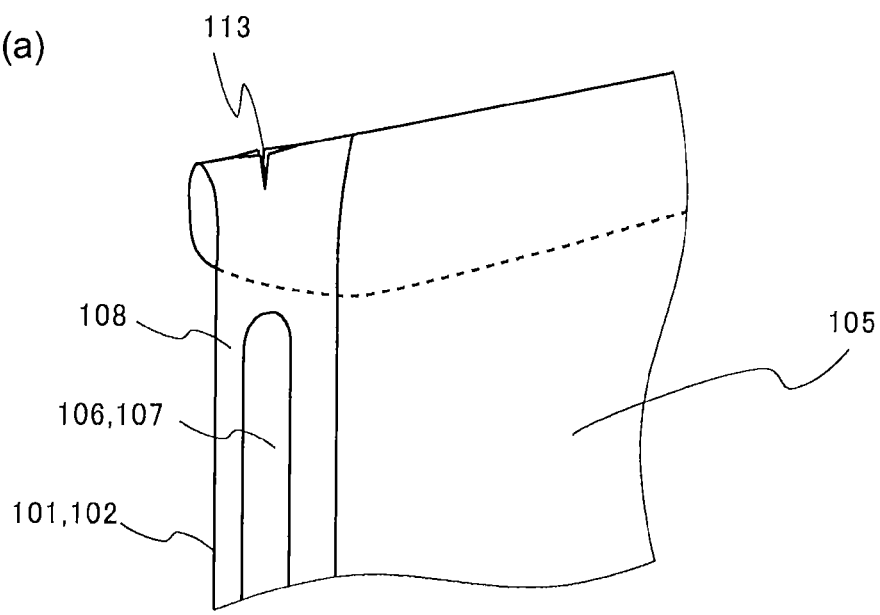
FIGS. 12(a) and 12(b) are diagrams illustrating a method of discharging gas from the flexible package.
Figure 12B:
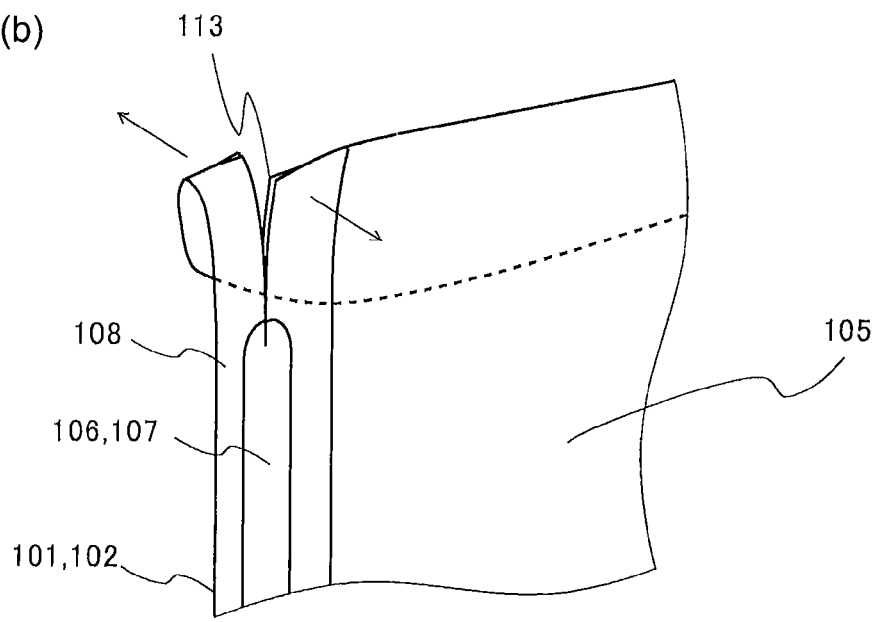
Figure 13:
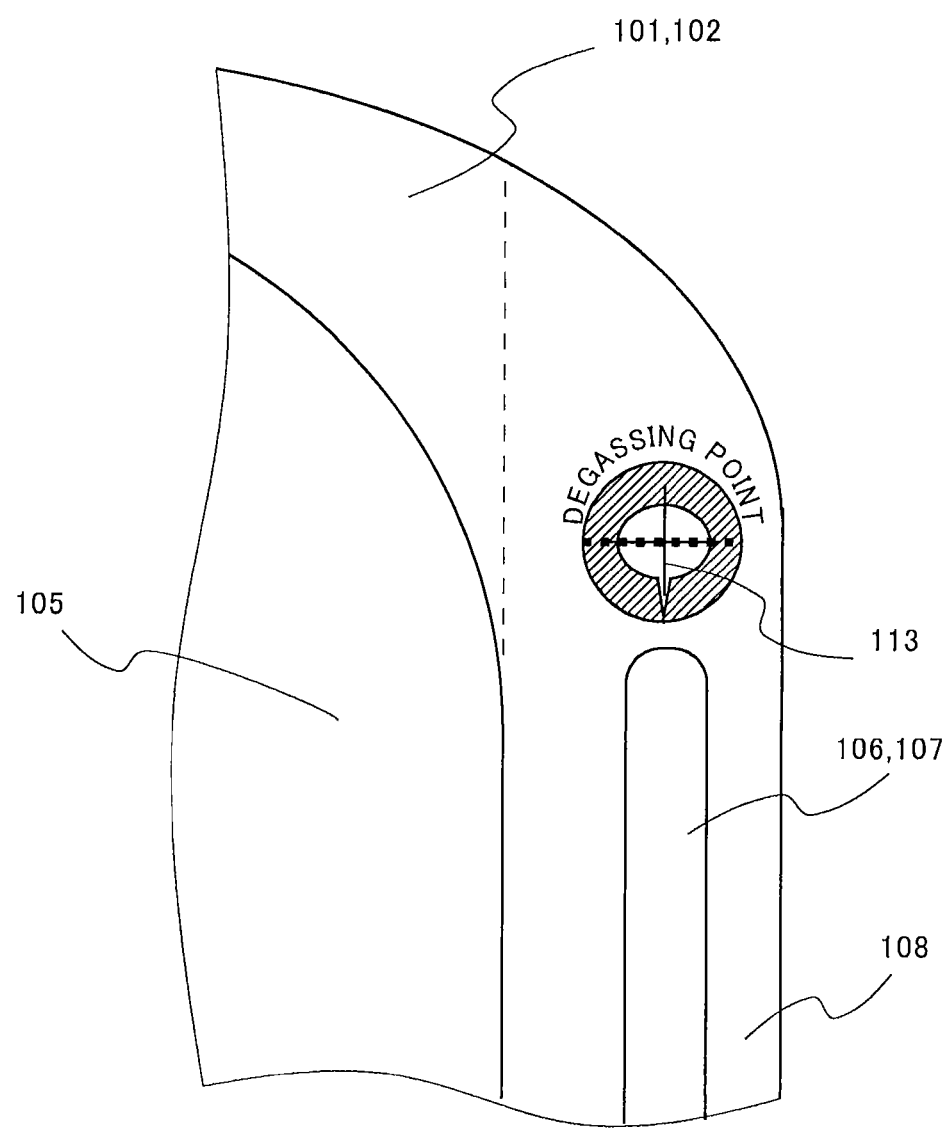
FIG. 13 is a partially enlarged view of a flexible package.

The flexible package 100 may have the following feature. That is, in the side edge portion 108, a cross-shaped slit 113 may be formed at a position near the gas injection portion 107, as a cut guide portion that guides cutting of the first side-surface film 101 and the second side-surface film 102 from the position to the gas injection portion 107. As shown in FIGS. 12(a), 12(b) and 13, the cross-shaped slit 113 is provided near the upper end of the gas injection portion 107, and is composed of two slit portions that penetrate the first side-surface film 101 and the second side-surface film 102 and extend in the left-right direction and the top-bottom direction, respectively.

The slit 113 is used for discharging the gas from the gas injection portion 107 when the flexible package 100 from which the contents have been taken out is rolled up. The procedure to discharge the gas will be described with reference to FIGS. 12(a) and 12(b). As shown in FIG. 12(a), the flexible package 100 is bent along the slit portion, of the slit 113, extending in the left-right direction. Thereby, the slit portion, of the slit 113, extending in the top-bottom direction is exposed on the fold line. Next, as shown in FIG. 12(b), the first side-surface film 101 and the second side-surface film 102 are torn from the slit portion, of the slit 113, extending in the top-bottom direction to extend the slit portion to the gas injection portion 107, thereby opening the gas injection portion 107. Thus, the gas in the gas injection portion 107 is discharged, and the flexible package 100 can be easily rolled up so as not to be bulky when it is discarded. In addition, since the flexible package 100 has to be bent before it is torn, the flexible package 100 is less likely to be accidentally torn from the slit 113 when it is normally handled.

The slit 113 is preferably provided at a position within 15 mm upward from the upper end of the gas injection portion 107 so that the extended slit easily reaches the gas injection portion 107. Further, of the slit 113, the slit portion in the left-right direction preferably has a length of 1 mm or more so as to facilitate bending of the flexible package 100, and the slit portion in the top-bottom direction preferably has a length of 1 mm or more so that the slit portion easily triggers tearing.

In at least one of the first side-surface film 101 and the second side-surface film 102, an indication that indicates the presence, position, or the like of the slit 113 is provided on or near the slit 113. In the example shown in FIG. 13, the position of the slit 113 as a degassing point is indicated by a circle and characters. In addition, a dotted line is provided along the slit portion, of the slit 113, in the left-right direction, which induces the user to bend the flexible package 100 along the dotted line. The indication is not limited to the above example, and may be implemented by various colors, figures, shapes, symbols, and the like. In addition to the indication, the above procedure of degassing may be described in detail at any position on the flexible package 100.

The slit 113 may be formed such that, in the process of producing the flexible package 100, the slit 111 and its vicinity are not sealed, i.e., are left non-fused.

Figure 14:
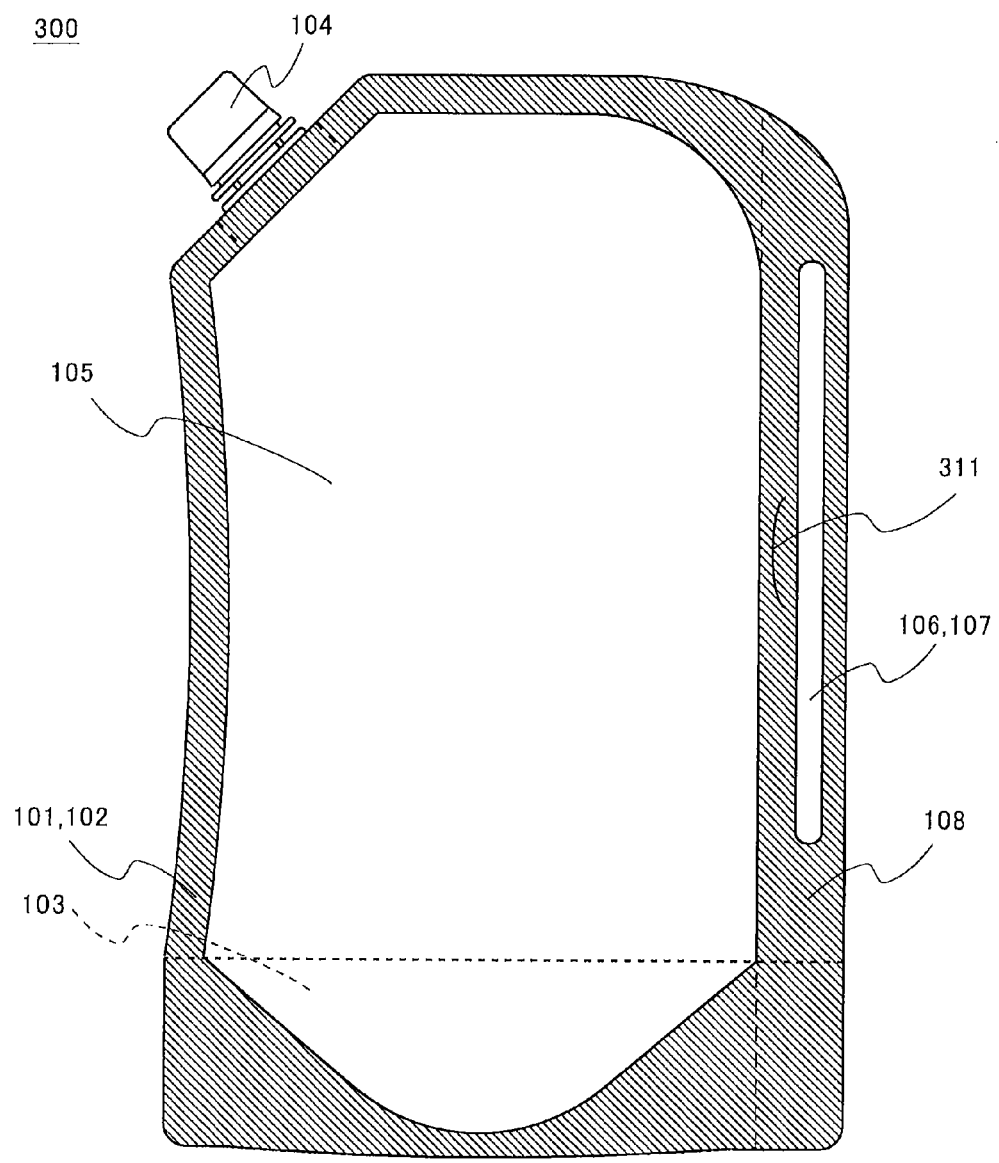
FIG. 14 is a plan view of a flexible package.
Figure 15A:
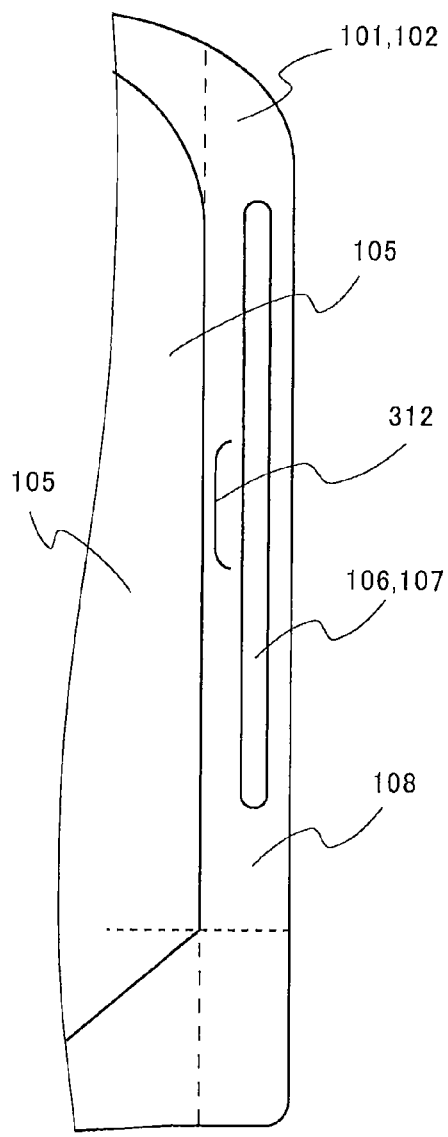
FIGS. 15(a) and 15(b) are partially enlarged views of the flexible package.
Figure 15B:
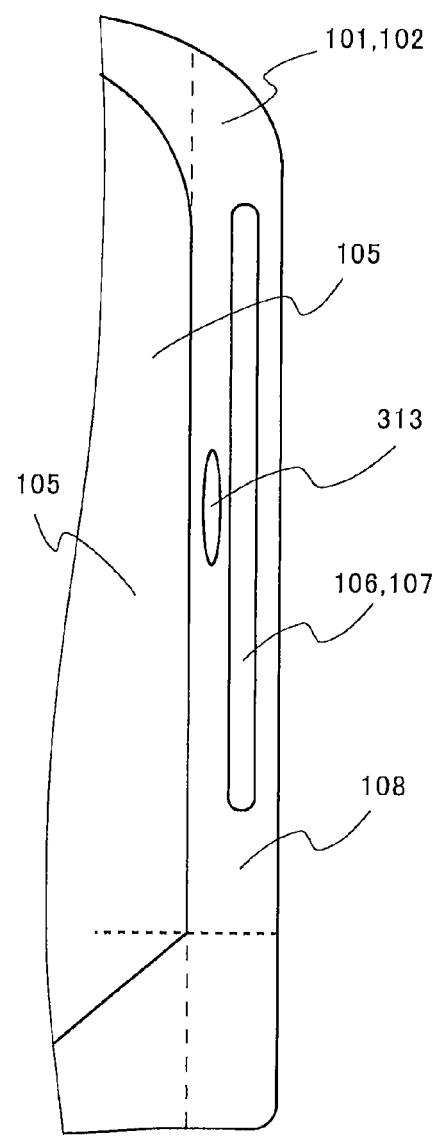

FIG. 14 shows a plan view of a flexible package 300 having another cut guide portion. The flexible package 300 is different from the flexible package 100 in the cut guide portion. In the flexible package 300, the cut guide portion is a slit 311 which is formed in a portion near the gas injection portion 107 on the storage part 105 side so as to penetrate the first side-surface film 101 and the second side-surface film 102. For example, the slit 311 is a curved line projecting toward the storage part 105 side. Another example of a slit is shown in FIG. 15(a). In the example shown in FIG. 15(a), a slit 312 has a shape composed of a straight line of a predetermined length extending in the top-bottom direction, and arcs extending from both ends of the straight line toward the gas injection portion 107. Instead of the slits 311 and 312, as shown in FIG. 15(b), a hole 313 may be formed by cutting an oval shape out of the first side-surface film 101 and the second side-surface film 102.

Figure 16A:
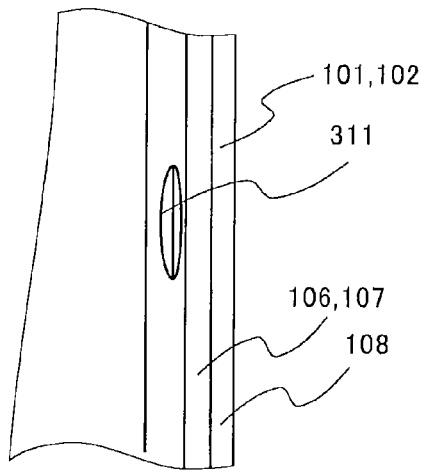
FIGS. 16(a)-16(c) are partially enlarged views of the flexible package.
Figure 16B:
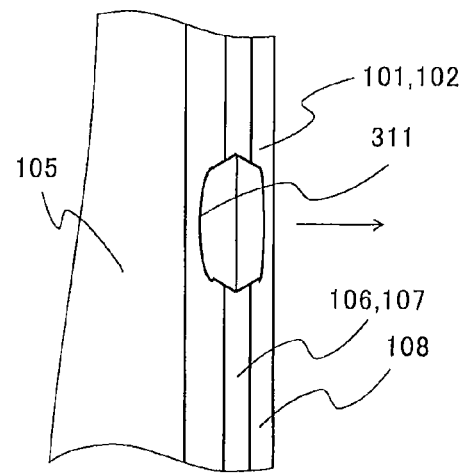
Figure 16C:
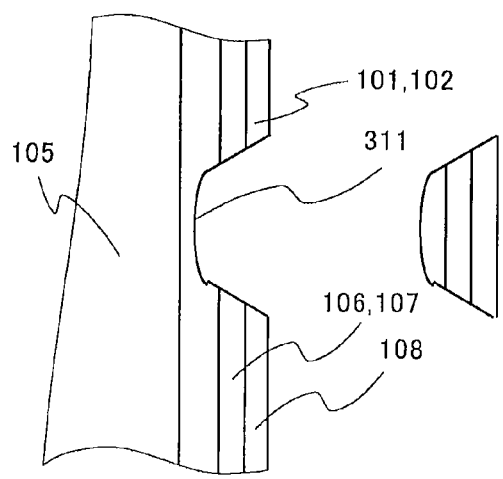

With reference to FIGS. 16(a)-16(c), the procedure to discharge the gas from the gas injection portion 107 of the flexible package 300 shown in FIG. 14 will be described. As shown in FIG. 16(a), first, a user inserts a finger in the slit 311, and bends the first side-surface film 101 and the second side-surface film 102. Next, as shown in FIG. 16(b), the user tears the first side-surface film 101 and the second side-surface film 102 from the slit 311 and extends the slit 311 to the gas injection portion 107, thereby opening the gas injection portion 107. The same applies to the case of providing the slit 312 shown in FIG. 15(a). Thereby, the gas in the gas injection portion 107 is discharged, and the flexible package 100 can be easily rolled up so as not to be bulky when it is discarded. In addition, since the first side-surface film 101 and the second side-surface film 102 need to be bent before they are torn, the flexible package 300 is less likely to be accidentally torn from the slit 311 when it is normally handled. Further, as shown in FIG. 16(c), the user may further extend the slit 311 to the outer edge of the flexible package 100, and tear off a portion of the flexible package 100 including a portion of the gas injection portion 107.

Also when the hole 313 is formed in the flexible package 300, the user inserts a finger in the hole 313, and tears the first side-surface film 101 and the second side-surface film 102 from the hole 313 to reach the gas injection portion 107, whereby the gas in the gas injection portion 107 can be discharged.

The slit 311 or the slit 312 is preferably formed to be close to the center portion of the gas injection portion 107 excluding the both ends thereof in the top-bottom direction, in order to enable more reliable tearing of the gas injection portion 107. In at least one of the first side-surface film 101 and the second side-surface film 102, an indication that indicates the presence, position, or the like of any of the slit 311, the slit 312, and the hole 313 may be performed on the slit (hole) or its vicinity.

Figure 17:
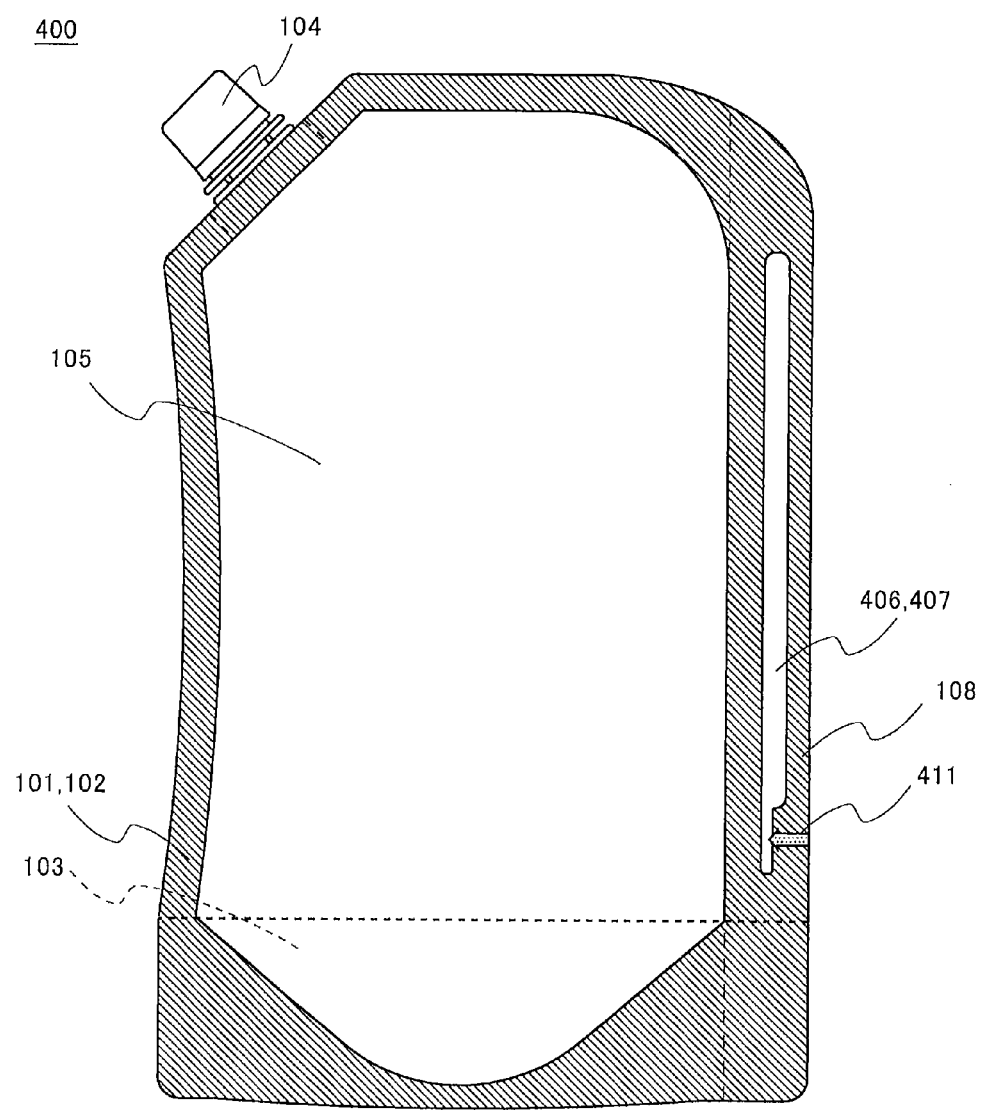
FIG. 17 is a plan view of a flexible package.

FIG. 17 shows a plan view of a flexible package 400 having another cut guide portion. The flexible package 400 is different from the flexible package 100 in the non-sealed region and the cut guide portion. In the flexible package 400, a non-sealed region 406, in a predetermined region including a lower end thereof, has a width of 3 mm or more in the left-right direction, and is 5 mm or more apart from the outer edge of the first side-surface film 101 and the second side-surface film 102. In addition, in the flexible package 400, a cut guide portion is an easy-to-cut portion 411 formed by arranging a plurality of fine flaws on the surface within a predetermined range, extending from the outer edge of the first side-surface film 101 and the second side-surface film 102 to the gas injection portion 407 formed in the predetermined region.

As shown in FIG. 18, when the first side-surface film 101 and the second side-surface film 102 are torn along the easy-to-cut portion 411 and the easy-to-cut portion 411 is extended to the gas injection portion 407, the gas injection portion 407 is opened, and thereby the gas is discharged from the gas injection portion 407. Thus, the flexible package 400 can be easily rolled up so as not to be bulky when it is discarded.

Since a portion of the non-sealed region 406 near the easy-to-cut portion 411 is 5 mm or more apart from the outer edge, the expanded gas injection portion 407 in this portion is apart from the outer edge. Therefore, a scratch work to form the flaws in the easy-to-cut portion 411 is easy to perform. In addition, the easy-to-cut portion 411 is easy to pinch, which makes tearing easy. In addition, since the portion of the non-sealed region 406 near the easy-to-cut portion 411 has a width of 3 mm or more in the left-right direction, spurious adhesion over the entire width is prevented, whereby the gas injection portion 407 can be formed with reliability. As shown in FIG. 17, the width of the non-sealed region 406 in the left-right direction, in a region other than the portion near the easy-to-cut portion 411, is preferably larger than the width thereof near the easy-to-cut portion 411 to make the gas injection portion 407 expand more.

Figure 19:
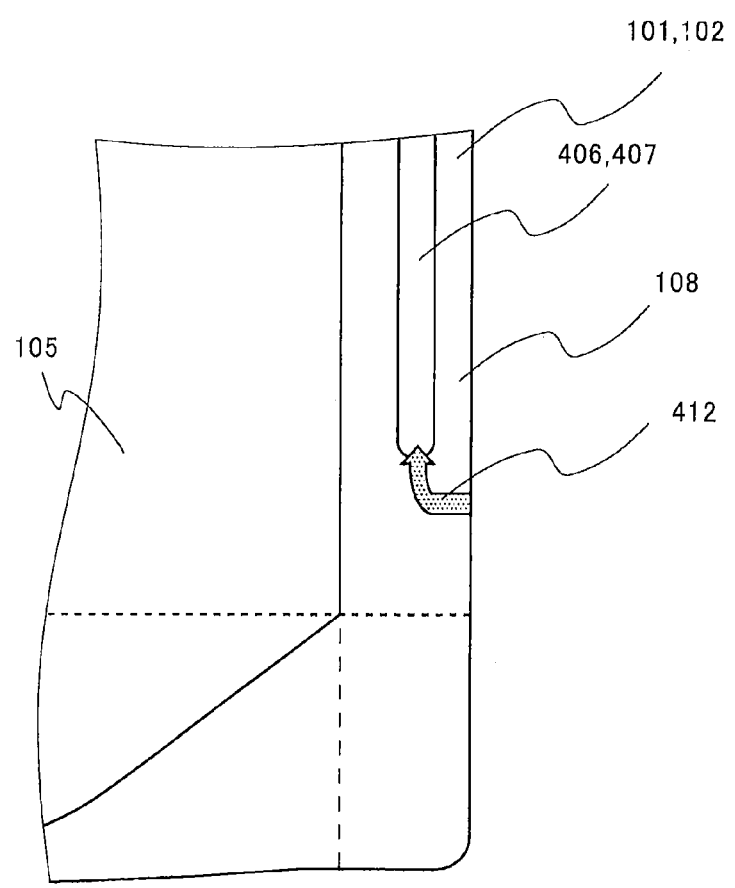
FIG. 19 is a partially enlarged view of the flexible package.

Alternatively, as shown in FIG. 19, the non-sealed region 406 may have a uniform width in the left-right direction, and an easy-to-cut portion 412 may be arranged in a curved region extending from the outer edge lower than the lower end of the gas injection portion 407 to the lower end of the gas injection portion 407.

The features of the flexible package according to the present invention have been described above. The flexible package may have all or part of the above-described features. It is apparent that a useful embodiment is achieved by any combination of the above-described features. In addition, the present invention is applicable not only to a self-standing flexible package having a bottom film but also to a flexible package that has no bottom film and is formed by joining a first side-surface film and a second side-surface film together. Also in this case, it is possible to improve portability of the flexible package, ease of discharging contents, and toughness against bending.

EXAMPLES

Hereinafter, examples, comparative examples, and evaluation results of the present invention will be described.

(Gas to be Injected into Gas Injection Portion)

Comparative Example 1-1 and Examples 1-2 to 1-5 of flexible packages 100, in which gas injection portions 107 were formed by injection of gases at 20° C. that were generated by mixing carbon dioxide and nitrogen at different ratios so as to have different specific heats at constant volume, were left for 30 minutes at 80° C. and observed. The observation result is shown in the following Table 1.

TABLE 1

|  |  | Specific heat at constant volume (0° C., 1 atm) | Observation result | Evaluation |
|---|---|---|---|---|
| Com. Exam. | 1-1 | 0.155 kcal/kg · deg<br>0.648 kJ/kg · deg | Peeling of seal<br>Gas leakage | − |
| Exam. | 1-2 | 0.160 kcal/kg · deg<br>0.669 kJ/kg · deg | Peeling of seal<br>No gas leakage | + |
|  | 1-3 | 0.165 kcal/kg · deg<br>0.690 kJ/kg · deg | Peeling of seal<br>No gas leakage | + |
|  | 1-4 | 0.170 kcal/kg · deg<br>0.711 kJ/kg · deg | No peeling of seal<br>No gas leakage | ++ |

TABLE 1-continued

| Specific heat at constant volume (0° C., 1 atm) | Observation result | Evaluation |
|---|---|---|
| 1-5 0.175 kcal/kg · deg<br>0.732 kJ/kg · deg | No peeling of seal<br>No gas leakage | ++ |

In Table 1, "++" indicates that the evaluation result was good, "+" indicates that the evaluation result was inferior to "++" but was within an allowable range, and "−" indicates that the evaluation result was not good. In Table 1, unit conversion of the specific heat at constant volume was performed with 1 cal=4.18 J.

In Comparative Example 1-1, peeling of the sealed portion near the gas injection portion 107 occurred. The peeling advanced up to the side edge of the flexible package 100, and the gas leaked to the outside from a gap between the first side-surface film 101 and the second side-surface film 102. In Examples 1-2 and 1-3, although peeling of the sealed portion occurred, the peeling did not advance up to the side edge of the flexible package 100, and no gas leakage was observed. In Examples 1-4 and 1-5, no peeling of the sealed portion occurred, and no gas leakage was observed.

From the above result, it was confirmed that no gas leakage occurs when the specific heat at constant volume of the gas inside the gas injection portion 107 is not lower than 0.160 kcal/kg·deg, i.e., not lower than about 0.67 kJ/kg deg. In addition, it was confirmed that no peeling of the sealed portion occurs even under the high temperature when the specific heat at constant volume is not lower than 0.170 kcal/kg·deg, i.e., not lower than about 0.71 kJ/kg·deg.

(Repelling Force of Gas Injection Portion)

Comparative Examples 2-1 and 2-2 and Examples 2-3 to 2-15 of flexible packages 100 were produced in which the diameter R of the gas injection portion 107 was 6 mm and the repelling force of the gas injection portion was varied, and were preserved for one month at 1 atm and at different temperatures of 23° C. (room temperature), 40° C., and 50° C. Then, the respective Comparative Examples and Examples were evaluated for stability of self-standing and ease of discharging contents. Each of Comparative Examples and Examples had a height of 282.5 mm, a width of 178 mm, and a capacity of 900 ml. The gas injection portion 107 was formed by injecting a gas into the non-sealed region 106 having a width of 10 mm, and had a cylindrical shape having a diameter R of 6 mm. The seal strength near the gas injection portion 107 was 110 N/15 mm. Each of Comparative Examples and Example was formed by using a laminate including polyethylene terephthalate, aluminum, nylon, and polyethylene. The evaluation result is shown in the following Table 2.

TABLE 2

|  | Com. Exam. | | Exam. | | | | | | | | | | | | |
|---|---|---|---|---|---|---|---|---|---|---|---|---|---|---|---|
|  | 2-1 | 2-2 | 2-3 | 2-4 | 2-5 | 2-6 | 2-7 | 2-8 | 2-9 | 2-10 | 2-11 | 2-12 | 2-13 | 2-14 | 2-15 |
| Repelling force (N) | 1 | 3 | 5 | 7 | 10 | 12 | 14 | 16 | 18 | 20 | 22 | 25 | 26 | 28 | 30 |
| 23° C. | − | − | + | ++ | ++ | ++ | ++ | ++ | ++ | ++ | ++ | ++ | ++ | ++ | ++ |
| 40° C. | − | − | + | ++ | ++ | ++ | ++ | ++ | ++ | ++ | ++ | ++ | ++ | ++ | − |
| 50° C. | − | − | + | ++ | ++ | ++ | ++ | ++ | ++ | ++ | ++ | ++ | ++ | − | − |

In Table 2, "++" indicates that the evaluation result was good. That is, since the gas injection portion 107 was less likely to bend, the flexible package was allowed to stably stand by itself. In addition, when the contents were discharged, the gas injection portion 107 was easy to hold, and it was easy to stabilize the direction of the discharge part 104, and therefore, it was easy to discharge the contents. Further, "+" indicates that the evaluation result was inferior to "++", but was within an allowable range. That is, although ease of discharging the contents could not be achieved, the flexible package was allowed to stably stand by itself. Further, "−" indicates that the evaluation result was not good. That is, the gas injection portion 107 was likely to bend, or gas leakage occurred, which did not contribute to stability of self-standing and ease of discharging the contents. Thus, the effect of providing the gas injection portion 107 could not be confirmed.

At any preservation temperature, Examples 2-4 to 2-13 (repelling force was not smaller than 7 N but not larger than 26 N) provided the good result, and Example 2-3 provided the result within the allowable range. Example 2-14 (repelling force was 28 N) provided the good result when it was preserved at 23° C. and 40° C. However, under preservation at 50° C., peeling of seal occurred extending from the gas injection portion 107 to the side edge of the flexible package 100, and gas leakage occurred. Example 2-15 (repelling force was 30 N) provided the good result when it was preserved at 23° C. However, under preservation at 40° C. and 50° C., peeling of seal and gas leakage similarly occurred. In Comparative Examples 2-1 and 2-2 (repelling force was 3 N or less), the gas injection portion 107 was likely to bend, and stable self-standing and ease of discharging the contents were not achieved.

Therefore, it was confirmed that, when the flexible package 100 is preserved at a room temperature of about 23° C., the repelling force is preferably not smaller than 4 N but not larger than 30 N (Examples), and more preferably, not smaller than 7 N but not larger than 30 N.

Further, it was confirmed that, when there is a possibility that the temperature of the gas injection portion 107 is 50° C. or more because high-temperature contents are injected or the package is left in high-temperature environment, the repelling force is preferably not smaller than 4 N but not larger than 26 N, and more preferably, not smaller than 7 N but not larger than 26 N.

In each of Comparative Examples 2-1 and 2-2 and Examples 2-3 to 2-15, the diameter R of the gas injection portion 107 was varied to 3 mm, 20 mm, and 50 mm, and thus obtained samples were preserved for one month at 1 atm and 50° C. Then, the respective Comparative Examples and Examples were evaluated for stability of self-standing and ease of discharging the contents. The evaluation result is shown in the following Table 3. In Table 3, the result obtained when the diameter R of the gas injection portion 107 is 6 mm is again shown for comparison.

TABLE 3

| | Com. Exam. | | Exam. | | | | | | | | | | | | |
|---|---|---|---|---|---|---|---|---|---|---|---|---|---|---|---|
| | 2-1 | 2-2 | 2-3 | 2-4 | 2-5 | 2-6 | 2-7 | 2-8 | 2-9 | 2-10 | 2-11 | 2-12 | 2-13 | 2-14 | 2-15 |
| Repelling force (N) | 1 | 3 | 5 | 7 | 10 | 12 | 14 | 16 | 18 | 20 | 22 | 25 | 26 | 28 | 30 |
| Diameter 3 mm | − | − | + | ++ | ++ | ++ | ++ | ++ | ++ | ++ | ++ | ++ | ++ | ++ | ++ |
| Diameter 6 mm | − | − | + | ++ | ++ | ++ | ++ | ++ | ++ | ++ | ++ | ++ | ++ | − | − |
| Diameter 20 mm | − | − | ++ | ++ | ++ | ++ | ++ | ++ | ++ | ++ | ++ | ++ | ++ | − | − |
| Diameter 50 mm | − | − | ++ | ++ | ++ | ++ | ++ | ++ | ++ | ++ | ++ | ++ | ++ | − | − |

In Table 3, the meanings of "++", "+" and "−" are similar to those in Table 2. With any diameter, the result was good when the repelling force was not smaller than 7 N but not larger than 26 N. When the repelling force was 28 N and 30 N, the result was good when the diameter R was 3 mm, but the result was not good because of gas leakage when the diameter was 6 mm or more. When the repelling force was 5 N, the result was within the allowable range when the diameter R was 3 mm and 6 mm, and the result was good when the diameter R was 20 mm and 50 mm. When the repelling force was 1 N and 3 N, the result was not good in both cases.

Further, it was confirmed that, when there is a possibility that the temperature of the gas injection portion 107 is 50° C. or more because high-temperature contents are injected or the package is left in high-temperature environment, the diameter R of the gas injection portion 107 is preferably set in a range from 3 mm to 50 mm, and the repelling force is preferably not smaller than 4 N but not larger than 26 N, and more preferably, not smaller than 7 N but not larger than 26 N.

(Rigidity of Side-Surface Films)

Flexible packages each having a spout shown in FIG. 1 were produced as Examples 3-2 to 3-8 and Comparative Examples 3-1 and 3-9. Each flexible package had a width (corresponding to W in FIG. 3) of 180 mm, and a height (corresponding to H in FIG. 3) of 280 mm. In each of Examples and Comparative Examples, a film having loop stiffness shown in the following Table 4 was used for the first side-surface film, the second side-surface film, and the bottom film.

FIG. 9 is a schematic diagram illustrating a loop stiffness measuring method. As a sample for loop stiffness measurement, a strip-shaped film having a width of 25 mm and a length of 120 mm was cut out from each of the same films as used for production of the flexible packages according to Examples and Comparative Examples. The strip-shaped film was cut out so that its longitudinal direction corresponded to the direction of the measurement target. The strip-shaped film was set on a loop stiffness tester manufactured by Toyo Seiki Kogyo Co., Ltd., and a loop was formed. A contact plate of the tester was pressed against the formed loop to squeeze the loop, and the repelling force of the loop was measured. The squeezing distance was 20 mm, and the compression rate was 3.5 mm/s. The value (mN) of the measured repelling force was regarded as the loop stiffness.

The evaluation criteria for self-standing property and formability are as follows:

(1) Self-Standing Property

++: The self-standing posture was maintained without hanging and bending of the upper part of the flexible package.

+: The self-standing posture was maintained although the upper part of the flexible package was slightly deformed.

−: The self-standing posture was not maintained because of hanging and bending of the upper part of the flexible package.

(2) Formability

++: The package forming processing was performed without any problem.

+: The easiness of the package forming processing was degraded due to the high stiffness of the film, but was not degraded to an extent that makes the package forming processing difficult.

−: The package forming processing was difficult due to the excessively high stiffness of the film.

Table 4 shows the values of the loop stiffnesses of the films used for Examples 3-2 to 3-8 and Comparative Examples 3-1 and 3-9, and the evaluation results of self-standing properties and formabilities of the flexible packages according to Examples 3-2 to 3-8 and Comparative Examples 3-1 and 3-9.

TABLE 4

| | | Loop stiffness (mN) | | Self- | |
|---|---|---|---|---|---|
| | | LSh (left-right direction) | LSv (up-down direction) | standing property | Formability |
| Com. Exam. | 3-1 | 0.4 | 0.1 | − | ++ |
| Exam. | 3-2 | 20 | 30 | + | ++ |
| | 3-3 | 80 | 80 | ++ | ++ |
| | 3-4 | 100 | 120 | ++ | ++ |
| | 3-5 | 145 | 145 | ++ | ++ |
| | 3-6 | 250 | 200 | ++ | ++ |
| | 3-7 | 550 | 480 | ++ | ++ |
| | 3-8 | 1200 | 1300 | ++ | + |
| Com. Exam. | 3-9 | 2000 | 2000 | ++ | − |

As shown in Table 4, it was confirmed that, in the flexible packages of Examples 3-2 to 3-8 which were each produced by using a film whose loop stiffness LSv in the top-bottom direction when the flexible package was self-standing was not smaller than 30 mN but not larger than 1300 mN and whose loop stiffness LSh in the left-right direction when the flexible package was self-standing was not smaller than 20 mN but not larger than 1200 mN, both the self-standing property and the formability were excellent. Further, it was confirmed that, in the flexible packages of Examples 3-3 to 3-7 which were each produced by using a film whose loop stiffness LSv was not smaller than 80 mN but not larger than 480 mN and whose loop stiffness LSh in the left-right direction when the flexible package was self-standing was not smaller than 80 mN but not larger than 550 mN, both the self-standing property and the formability were superior to those of Examples 3-2 to 3-8.

In contrast, it was confirmed that the flexible package according to Comparative Example 3-1 was insufficient in the self-standing property, and the flexible package according to Comparative Example 3-9 was inferior in formability.

(Gas Barrier Property)

Flexible packages each having a spout shown in FIG. 1 were produced as Examples 4-1 to 4-4 and Comparative Example 4-5. The width (corresponding to W in FIG. 3) of each flexible package was 180 mm, and the height (corresponding to H in FIG. 3) thereof was 280 mm. In Examples 4-1 to 4-4 and Comparative Example 4-5, layer structures of films used for the first side-surface film, the second side-surface film, and the bottom film are as follows. In each layer structure, a numerical value in parenthesis represents the thickness of each layer.

Example 4-1

A film obtained by laminating, in order from the side to be an outer surface, polyethylene terephthalate (12 μm)/aluminum foil (9 μm)/nylon (15 μm)/LLDPE; Linear Low Density Polyethylene (100 μm) was used.

Example 4-2

A film obtained by laminating, in order from the side to be an outer surface, a transparent deposition gas barrier film (12 μm)/nylon (15 μm)/CPP; unstretched polypropylene (70 μm) was used. As the transparent deposition gas barrier film of Example 4-2, a polyethylene terephthalate film having, on one surface thereof, a vapor-deposited inorganic oxide (aluminum oxide) film was used. The film was structure so that the vapor-deposited inorganic oxide film was positioned on the nylon side.

Example 4-3

A film obtained by laminating, in order from the side to be an outer surface, nylon (15 μm)/aluminum deposition gas barrier film (12 μm)/LLDPE; Linear Low Density Polyethylene (100 μm) was used. As the aluminum deposition gas barrier film of Example 4-3, a polyethylene terephthalate film having, on one surface thereof, a vapor-deposited aluminum film was used. The film was structure so that the vapor-deposited aluminum film was positioned on the nylon side.

Example 4-4 a film obtained by laminating, in order from the side to be the outer surface, polyethylene terephthalate (12 μm)/nylon (15 μm)/LLDPE; Linear Low Density Polyethylene (100 μm) was used.

Comparative Example 4-5 a film obtained by laminating, in order from the side to be an outer surface, polyethylene terephthalate (12 μm)/LLDPE; Linear Low Density Polyethylene (120 μm) was used.

The flexible packages according to Examples 4-1 to 4-4 and Comparative Example 4-5 were formed using the above-described films so that the non-sealed region 106 was filled with air and hermetically sealed, and were preserved under the conditions shown in the following Table 5.

After the preservation period has passed, the state of each gas injection portion was evaluated for any of "++", "+", and "−", according to the following evaluation criteria.

++: No or almost no discharge of air from the gas injection portion was observed. As compared to the state immediately after air injection, the shape retaining property of the flexible package and the ease of holding as a handle were not changed.

+: Although some air was discharged from the gas injection portion, the shape retaining property of the flexible package and the ease of holding as a handle were sufficiently maintained as compared to the state immediately after air injection.

−: Discharge of air from the gas injection portion was significant, and the gas injection portion was bent. Thus, the shape retaining property and the function as a handle were deteriorated.

Table 5 shows oxygen permeabilities of the non-sealed regions of the flexible packages according to Examples 4-1 to 4-4 and Comparative Example 4-5, and evaluation results under different preservation conditions.

TABLE 5

| | | | Preservation condition | | |
|---|---|---|---|---|---|
| | | Oxygen permeability cc/(m² · day · atm) | 20° C., 1 year | 40° C., 6 months | 60° C., 1 month |
| Exam. | 4-1 | 0 | ++ | ++ | ++ |
| | 4-2 | 0.5 | ++ | ++ | ++ |
| | 4-3 | 1 | ++ | ++ | ++ |
| | 4-4 | 30 | + | + | + |
| Com. Exam. | 4-5 | 100 | − | − | − |

In the flexible package according to Comparative Example 4-5, discharge of air from the gas injection portion was significant, and the gas injection portion was bent and the upper part of the flexible package hung down due to the weight of the contents, and thus the shape of the flexible package was not maintained. In addition, since the inner pressure of the gas injection portion was greatly reduced, the gas injection portion was bent when the user held the gas injection portion. Thus, the function as a handle was insufficient, and it was difficult to discharge the contents.

In contrast, as shown in the evaluation result in Table 5, in each of the flexible packages according to Examples 4-1 to 4-4, the inner pressure of the gas injection portion was not reduced to the extent that the upper part of the flexible package hung down, and thus the shape retaining property was maintained. In the flexible packages according to Examples 4-1 to 4-4, since reduction in the inner pressure of the gas injection portion was suppressed, the function of the gas injection portion as a handle was not deteriorated. Even after the preservation period has passed, ease of discharging the contents with the gas injection portion and its vicinity being held was maintained. In particular, in the flexible packages of Examples 4-1 to 4-3 in which the oxygen permeability of the non-sealed region was 5 cc/(m²·day·atm), discharge of air immediately after injection of air into the non-sealed region was not observed, and the inner pressure of the gas injection portion was maintained at the same level as that immediately after air injection, whereby the shape retaining property and the function as a handle were maintained for a long period of time.

(Seal Strength)

Examples 5-2 to 5-5, 5-7, 5-8, and 5-10 to 5-12 and Comparative Examples 5-1, 5-6 and 5-9 of the flexible package 100 in which the diameter R of the gas injection portion 107 was 8 mm and the length thereof was 180 mm were produced. In each of Comparative Examples and Examples, the height was 280 mm, the width was 180 mm, and the insertion length of the bottom film 103 was 50 mm. One gas injection portion 107 was provided in the side edge portion 108. The width of the side edge portion 108 in which the gas injection portion 107 was formed was 22 mm. Each of Comparative Example 5-1 and Examples 5-2 to 5-5 was formed of a film having a layer structure of PET (polyethylene terephthalate) of 12 μm/aluminum (AL) of 9 μm/nylon (NY) of 15 μm/linear low density polyethylene (LLDPE) of 100 μm. Each of Comparative Example 5-6 and Examples 5-7 and 5-8 was formed of a film having a layer structure of transparent deposition PET of 12 μm/NY of 15 μm/unstretched polypropylene (CPP) of 70 μm. The transparent deposition PET is a transparent film having barrier property and obtained by vapor-depositing alumina, silicon oxide, or the like on a PET film. Each of Comparative Example 5-9 and Examples 5-10 to 5-12 was formed of a film having a layer structure of NY of 15 μm/AL deposition PET of 12 μm/LLDPE of 100 μm.

The seal strength of the side edge portion 108 in which the gas injection portion 107 is formed is 20 N/15 mm in Comparative Examples 5-1, 5-6 and 5-9, 30 N/15 mm in Examples 5-2, 5-7 and 5-10, 50 N/15 mm in Examples 5-3, 5-8 and 5-11, 80 N/15 mm in Example 5-12, 100 N/15 mm in Example 5-4, and 150 N/15 mm in Example 5-5. In each of Examples and Comparative Examples, presence/absence of gas leakage due to peeling of seal was checked: at the time of gas injection when the gas injection portion 107 was formed so that the above-described repelling force was 10 N and 30 N at room temperature and 1 atm; at the time of boiling when, after formation of the gas injection portion 107, the gas injection portion 107 was heated for 60 minutes in hot water of 95° C. at 1 atm; and at the time of high-temperature preservation when the gas injection portion 107 was preserved for one week in air at 60° C. and 1 atm. The result is shown in the following Table 6.

TABLE 6

|  |  | Seal strength (N/15 mm) | Repelling force of gas injection portion 10N | | | Repelling force of gas injection portion 30N | | |
|---|---|---|---|---|---|---|---|---|
|  |  |  | Gas injection | Boiling | High-tem. preservation | Gas injection | Boiling | High-tem. preservation |
| Com. Exam. | 5-1 | 20 | + | − | − | − | NA | NA |
| Exam. | 5-2 | 30 | + | + | + | + | + | + |
|  | 5-3 | 50 | + | + | + | + | + | + |
|  | 5-4 | 100 | + | + | + | + | + | + |
|  | 5-5 | 150 | + | + | + | + | + | + |
| Com. Exam. | 5-6 | 20 | + | − | − | − | NA | NA |
| Exam. | 5-7 | 30 | + | + | + | + | + | + |
|  | 5-8 | 50 | + | + | + | + | + | + |
| Com. Exam. | 5-9 | 20 | + | − | − | − | NA | NA |
| Exam. | 5-10 | 30 | + | + | + | + | + | + |
|  | 5-11 | 50 | + | + | + | + | + | + |
|  | 5-12 | 80 | + | + | + | + | + | + |

In Table 6, "+" indicates that no gas leakage occurred, and "−" indicates that gas leakage occurred. In Comparative Examples 5-1, 5-6, and 5-9 in which the seal strength was 20 N/15 mm, no gas leakage occurred at the time of gas injection, but gas leakage occurred at the time of boiling and high-temperature preservation. When the repelling force was 30 N, gas leakage occurred at the time of gas injection, and no gas injection portion 107 was formed. Therefore, evaluations at the time of boiling and high-temperature preservation could not be performed (NA). In contrast, in each of Examples having the seal strength of 30 N/15 mm, in either case where the repelling force was 10N or 30N, no gas leakage occurred during any of gas injection, boiling, and high-temperature preservation.

When each of Examples and Comparative Example were caused to fall fast, peeling of seal was confirmed in an extremely small part of the side edge portion 108 in Comparative Example 5-1, Example 5-2, Comparative Example 5-6, Example 5-7, Comparative Example 5-9, and Example 5-10 in which the seal strength was 30 N/15 mm or less, but no peeling of seal occurred in Examples 5-3, 5-4, 5-5, 5-8, 5-11 and 5-12 in which the seal strength was 50 N/15 mm or more. Thus, sufficient strength was confirmed.

(Shape)

A plurality of blanks similar to the blank 200 shown in FIG. 11 were produced in which the width W and the insertion length B of the bottom film 103 were varied. In each blank, contents were injected into the storage part 105, gas was injected into the non-sealed region 106 to form the gas injection portion 107, and the storage part 105 and the slit 111 were sealed, thereby producing a sample of a flexible package. Each sample was evaluated for ease of self-standing and expansion of the bottom film 103. The evaluation result is shown in the following Table 7.

TABLE 7

|  |  | W (mm) |  |  | Self- | Expansion |  |
|---|---|---|---|---|---|---|---|
|  | Ratio (B/W) | 170 | 140 | 110 | standing property | of bottom film | Overall evaluation |
|  |  |  | B (mm) |  |  |  |  |
| Com. Exam. | 6-1 | 0.10 | 17 | 14 | 11 | − | ++ | − |
| Exam. | 6-2 | 0.15 | 26 | 21 | 17 | + | ++ | + |
|  | 6-3 | 0.20 | 34 | 28 | 22 | ++ | ++ | ++ |
|  | 6-4 | 0.25 | 43 | 35 | 28 | ++ | ++ | ++ |
|  | 6-5 | 0.30 | 51 | 42 | 33 | ++ | ++ | ++ |
|  | 6-6 | 0.35 | 60 | 49 | 39 | ++ | ++ | ++ |
|  | 6-7 | 0.40 | 68 | 56 | 44 | ++ | + | + |
|  | 6-8 | 0.45 | 77 | 63 | 50 | ++ | + | + |
| Com. Exam. | 6-9 | 0.50 | 85 | 70 | 55 | ++ | − | − |
|  | 6-10 | 0.55 | 94 | 77 | 61 | ++ | − | − |
|  | 6-11 | 0.60 | 102 | 84 | 66 | ++ | − | − |

In Table 7, samples corresponding to Examples 6-2 to 6-8 each have the above-described second feature, whereas samples corresponding to Comparative Examples 6-1, 6-9 to 6-11 each do not have the second feature. In Table 7, "++" indicates that the evaluation result was good, "+" indicates that the evaluation result was inferior to "++" but was within an allowable range, and "−" indicates that the evaluation result was not good. In Examples 6-2 to 6-8, the first side-surface film 101 and the second side-surface film 102 were sufficiently expanded in a cylindrical shape and stably stood up, and the fold line of the bottom film 103 was sufficiently extended in the center portion thereof to make the bottom surface of the storage part 105 flat, and thereby a sufficient capacity of the storage part 105 was ensured. In addition, within a range of 0.20≤B/W<0.35, the stability of self-standing and the expansion of the bottom film were particularly good. In contrast, in Comparative Example 6-1 whose ratio of B/W is smaller than those of Examples 6-2 to 6-8, the first side-surface film 101 and the second side-surface film 102 were not expanded in a cylindrical shape, and were difficult to stably stand up. In Comparative Examples 6-9 to 6-11 whose ratios of B/W were larger than those of Examples 6-2 to 6-8, the folded bottom film 103 was not sufficiently extended and therefore the bottom surface of the storage part 105 was not made flat, and thus a sufficient capacity of the storage part 105 could not be ensured.

Further, blanks similar to the blank 120 shown in FIG. 3 were produced in which the distance from the upper end of the non-sealed region 106 to the upper end of the blank 120 was varied. In each blank, water was injected as contents into the storage part 105, and gas was injected into the non-sealed region 106 to form the gas injection portion 107, and then the storage part 105 and the slit 111 were sealed, thereby producing Examples 7-1, 7-2 and 7-5 and Comparative Examples 7-3, 7-6 and 7-7 of flexible packages. The height H of each of Examples and Comparative Examples was 280 mm, and the width W thereof was 180 mm. The insertion length B of the bottom film 103 was 50 mm, and the distance D from the lower end of each flexible package to the lower end of the gas injection portion 107 was 80 mm. In Examples 7-1 and 7-2 and Comparative Example 7-3, the distance A from the upper end of the gas injection portion 107 to the upper end of the flexible package 100 was 60 mm, 80 mm, and 100 mm, respectively. Meanwhile, Comparative Examples 7-4 and 7-8 were also produced in which water was injected into the blank 120 and the storage part 105 was sealed, but no gas injection portion 107 was formed. In Examples 7-1 and 7-2 and Comparative Examples 7-3 and 7-4, 900 ml of water was injected so that the distance C from the water surface to the upper end of the flexible package 100 was 80 mm. In Example 7-5 and Comparative Examples 7-6 to 7-8, 1000 ml of water was injected so that the distance C from the water surface to the upper end of the flexible package 100 was 65 mm. The respective Examples and Comparative Examples were evaluated for ease of retaining the self-standing posture and ease of discharge. The evaluation result is shown in the following Table 8.

TABLE 8

|  |  | A (mm) | A/H (%) | C (mm) | Self-standing property | Ease of discharge |
|---|---|---|---|---|---|---|
| Exam. | 7-1 | 60 | 21 | 80 | ++ | ++ |
|  | 7-2 | 80 | 29 | 80 | ++ | ++ |
| Com. Exam. | 7-3 | 100 | 36 | 80 | − | − |
|  | 7-4 | NA | NA | 80 | − | − |
| Exam. | 7-5 | 60 | 21 | 65 | ++ | ++ |
| Com. Exam. | 7-6 | 80 | 29 | 65 | − | ++ |
|  | 7-7 | 100 | 36 | 65 | − | − |
|  | 7-8 | NA | NA | 65 | − | − |

In Table 8, each of Examples 7-1, 7-2 and 7-5 and Comparative Examples 7-3, 7-4 and 7-6 to 7-8 has a B/W ratio of 0.28, and has the second feature. Each of Examples 7-1, 7-2 and 7-5 has the fourth feature and the fifth feature. Comparative Example 7-6 has the fourth feature but does not have the fifth feature. Each of Comparative Examples 7-3, 7-4, 7-7 and 7-8 do not have the fourth and fifth features. In Table 8, "++" indicates that the evaluation result was good, and "−" indicates that the evaluation result was not good. In Examples 7-1, 7-2 and 7-5, it was confirmed that, when the upper part of the flexible package 100 was bent, the flexible package 100 was restored to the original shape, and the shape was less likely to deform, and thus the self-standing property was easily maintained. In Comparative Examples 7-3, 7-4 and 7-6 to 7-8, the upper part of the flexible package 100 was bent and the shape was deformed to be easy to fall, and thus the self-standing property was not sufficiently maintained. In Examples 7-1, 7-2 and 7-5 and Comparative Example 7-6, when water was discharged from the discharge part 104, the upper part of the flexible package 100 was not bent, and the discharge part 104 can be stably directed to the discharge direction, and thus satisfactory ease of discharge was achieved. However, in Comparative Examples 7-3, 7-4, 7-7 and 7-8, the upper part of the flexible package was bent when water was discharged, and the discharge part 104 could not be directed in the discharge direction, and thus sufficient ease of discharge could not be obtained.

A bottom gusset type flexible package having a large size or including a spout or the like attached to an opening portion is low in rigidity. Therefore, when such a flexible package is displayed or used on a table, an upper portion thereof may be bent to deteriorate appearance of the package, or the package may lose the self-standing property and fall. Further, when such a flexible package is held up to discharge the contents out of the package, the package is likely to bend, and therefore, it is difficult to hold the package or discharge the contents. Therefore, an object of the present invention is to solve the above-described problems by improving the shape retaining property of the flexible package, and improving the self-standing property thereof. In order to solve the above problems, the present invention provides a flexible package in which at least a first side-surface film and a second side-surface film are joined together, and peripheral portions of the films are sealed to form a storage part. On one or both of two side edge portions which are sealed regions of the peripheral portions at both side ends of the first side-surface film and the second side-surface film, a non-sealed region is provided which is a region in which the first side-surface film and the second side-surface film are not sealed over a predetermined length. The non-sealed region is surrounded by the sealed regions of the first side-surface film and the second side-surface film. In the non-sealed region, a gas injection portion is formed in which a gas whose specific heat at constant volume is 0.67 kJ/kg·deg or higher at 0° C. and 1 atm. The gas injection portion has a diameter not smaller than 3 mm but not larger than 50 mm. A repelling force measured when the entirety of the gas injection portion is nipped from the first side-surface film side and the second side-surface film side and squeezed until the width of the nipped gas injection portion becomes half the diameter of the gas injection portion, is not smaller than 4 N but not larger than 30 N at 23° C. and 1 atm.

Further, the flexible package further includes a bottom film which is folded in half and inserted, from a fold line side, between the first side-surface film and the second side-surface film, and has a sealed peripheral portion. A loop stiffness of the first side-surface film and the second side-surface film in a direction corresponding to a vertical direction when the flexible package is made to stand by itself with the bottom film side as a bottom surface, is not smaller than 30 mN but not larger than 1300 mN. A loop stiffness of the first side-surface film and the second side-surface film in a direction corresponding to a horizontal direction when the flexible package is made to stand by itself, is not smaller than 20 mN/25 mm (width) but not larger than 1200 mN/25 mm (width).

The non-sealed region may have an oxygen permeability equal to or lower than 30 cc/(m²·day·atm) at 20° C. and 60%.

The side edge portions each may have a seal strength equal to or larger than 30 N/15 mm.

A distance from an upper end of the non-sealed region to an upper end of the flexible package may be equal to or smaller than 30% of a height of the flexible package.

In the side edge portions, a cut guide portion may be formed at a position near the gas injection portion so as to extend from the position to the gas injection portion. The cut guide portion guides cutting of the first side-surface film and the second side-surface film.

According to the present invention, it is possible to provide a flexible package including a gas injection portion which improves self-standing property and portability of the flexible package.

The present invention is useful for flexible packages and the like.

Obviously, numerous modifications and variations of the present invention are possible in light of the above teachings. It is therefore to be understood that within the scope of the appended claims, the invention may be practiced otherwise than as specifically described herein.

What is claimed is:
1. A flexible package, comprising:
a first side-surface film, a second side-surface film, and a bottom film which are joined together, the bottom film being inserted between the first side-surface film and the second side-surface film so as to be folded in half and inserted from a fold line side, with a predetermined insertion length; and
a storage part formed by sealing peripheral portions of the films excluding a portion through which contents are to be injected, the storage part having a lower bottom surface which is the bottom film,
wherein
on only one of two side edge portions which are sealed regions of the peripheral portions at both side ends of the first side-surface film and the second side-surface film, a non-sealed region is provided which is surrounded by the sealed regions and is not sealed over a predetermined length in a top-bottom direction,
the non-sealed region has a uniform diameter of 3 to 50 mm,
regarding the non-sealed region, a distance, along an extending direction of the non-sealed region, from an upper end of the non-sealed region to an upper end portion of the flexible package where an end portion of the first side-surface film and an end portion of the second side-surface film overlap each other, in a state where the first side-surface film and the second side-surface film are flat, is less than or equal to 30% of a height of the flexible package which is a distance from a lower end of the bottom film to the upper end portion along the extending direction of the non-sealed region, in the state where the first side-surface film, the second side-surface film, and the bottom film are flat,
at an upper end of the other one of the two side edge portions of the flexible package, a discharge part is provided such that a lower end thereof is located beneath the upper end of the non-sealed region, along the extending direction of the non-sealed region, in the state where the first side-surface film and the second side-surface film are flat, and
the storage part is separated from the non-sealed region by the sealed regions having a predetermined width.
2. The flexible package according to claim 1, wherein
a slit or a hole penetrating at least one of the first side-surface film and the second side-surface film is formed near the upper end of the non-sealed region, a distance from a lower end of the slit or the hole to the upper end portion of the flexible package along the extending direction of the non-sealed region is less than or equal to 30% of the height of the flexible package, in the state where the first side-surface film and the second side-surface film are flat, and the discharge part is provided such that the lower end thereof is located beneath the lower end of the slit or the hole along the extending direction of the non-sealed region, in the state where the first side-surface film and the second side-surface film are flat.

3. The flexible package according to claim 1, wherein the discharge part is a sealed spout sandwiched between the first side-surface film and the second side-surface film.

4. The flexible package according to claim 1, wherein a distance between a lower end of the non-sealed region and the fold line of the bottom film is larger than a length, along the fold line, of the sealed region of the side edge portion at a side at which the non-sealed region is provided.

5. The flexible package according to claim 1, wherein the sealed region has, between the non-sealed region and the storage part, an arch shaped section having a curved edge at a boundary with the storage part that projects toward the storage part.

6. The flexible package according to claim 1, wherein the sealed region has, between the non-sealed region and the storage part, a middle section having a greater width between the storage part and the non-sealed region than a width between the storage part and the gas injection portion of sections above and below the middle section.

7. A flexible package, comprising:
a first side-surface film, a second side-surface film, and a bottom film which are joined together, the bottom film being inserted between the first side-surface film and the second side-surface film so as to be folded in half and inserted from a fold line side, with a predetermined insertion length; and
a storage part formed by sealing peripheral portions of the films, the storage part having a lower bottom surface which is the bottom film,
wherein
on only one of two side edge portions which are sealed regions of the peripheral portions at both side ends of the first side-surface film and the second side-surface film, a gas injection portion is provided which is surrounded by the sealed regions, is not sealed over a predetermined length in a top-bottom direction, and is formed by a gas injected therein,
regarding the gas injection portion, a distance, along an extending direction of the gas injection portion, from an upper end of the gas injection portion to an upper end portion of the flexible package where an end portion of the first side-surface film and an end portion of the second side-surface film overlap each other, in a state where the first side-surface film and the second side-surface film are flat, is less than or equal to 30% of a height of the flexible package which is a distance from a lower end of the bottom film to the upper end portion along the extending direction of the gas injection portion, in the state where the first side-surface film, the second side-surface film, and the bottom film are flat, and
in the storage part, contents are injected to a height that does not exceed the upper end of the gas injection portion, in a vertical direction when the flexible package stands by itself, at an upper end of the other one of the two side edge portions of the flexible package, a discharge part is provided, the gas injection portion has a uniform diameter of 3 to 50 mm, a force required for nipping the gas injection portion from the first side-surface film side and the second side-surface film side by means of flat surfaces of two jigs so as to cover the entirety of the gas injection portion, and for squeezing the gas injection portion until a width of the nipped gas injection portion becomes half the diameter of the gas injection portion, is not smaller than 7 N but not larger than 30 N at 23° C. and 1 atm, and the storage part is separated from the gas injection portion by a sealed region having a predetermined width.

8. The flexible package according to claim 7, wherein in the side edge portions, a cut guide portion to guide cutting of the first side-surface film and the second side-surface film is formed at a position near the gas injection portion so as to extend from the position to the gas injection portion, the cut guide portion being at least one slit extending in a top-bottom direction and penetrating the first side-surface film and the second side-surface film.

9. The flexible package according to claim 8, wherein in at least one of the first side-surface film and the second side-surface film, an indication that indicates the position of the cut guide portion is provided on or near the cut guide portion.

10. The flexible package according to claim 8, wherein the cut guide portion is a cross-shaped slit which is formed at a position within 15 mm upward from an upper end of the gas injection portion, and is composed of a slit extending in the top-bottom direction, and a slit extending in a left-right direction and penetrating the first side-surface film and the second side-surface film, and the slit extending in the top-bottom direction and the slit extending in a left-right direction each have a length not smaller than 1 mm.

11. The flexible package according to claim 7, further comprising:
a sealed spout sandwiched between the first side-surface film and the second side-surface film.

12. The flexible package according to claim 7, wherein a distance between a lower end of the gas injection portion and the fold line of the bottom film is larger than a length, along the fold line, of the sealed region of the side edge portion at a side at which the gas injection portion is provided.

13. The flexible package according to claim 7, wherein the sealed region has, between the gas injection portion and the storage part, an arch shaped section having a curved edge at a boundary with the storage part that projects toward the storage part.

14. The flexible package according to claim 7, wherein the sealed region has, between the gas injection portion and the storage part, a middle section having a greater width between the storage part and the gas injection portion than a width between the storage part and the gas injection portion of sections above and below the middle section.

15. A flexible package having a self-standing property, comprising:
at least a first side-surface film and a second side-surface film, having sealed peripheral portions thereof; and
a storage part surrounded by the sealed peripheral portions; wherein
on only one of two side edge portions which are sealed regions of the peripheral portions at both side ends of the first side-surface film and second side-surface film, a gas injection portion is provided which is surrounded by the sealed regions and is not sealed over a predetermined length in a top-bottom direction, and that has a gas injected therein; and at an upper end of the other one of the two side edge portions, a discharge part is provided, the gas injection portion has a uniform diameter of 3 to 50 mm, a force required for nipping the gas injection portion from the first side-surface film side and the second side-surface film side by means of flat surfaces of two jigs so as to cover the entirety of the gas injection portion, and for squeezing the gas injection portion until a width of the nipped gas injection portion becomes half the diameter of the gas injection portion, is not smaller than 7 N but not larger than 30 N at 23° C. and 1 atm, and a handle of the flexible package is formed by being separated by the sealed portion having a predetermined width from the storage part.

16. The flexible package according to claim 15, further comprising a bottom film inserted between the first side-surface film and the second side-surface film so as to be folded in half and inserted from a fold line side, with a predetermined insertion length, wherein a distance between a lower end of the gas injection portion and the fold line of the bottom film is larger than a length, along the fold line, of the sealed region of the side edge portion at a side at which the gas injection portion is provided.

17. The flexible package according to claim 15, wherein the sealed region has, between the gas injection portion and the storage part, an arch shaped section having a curved edge at a boundary with the storage part that projects toward the storage part.

18. The flexible package according to claim 15, wherein the sealed region has, between the gas injection portion and the storage part, a middle section having a greater width between the storage part and the gas injection portion than a width between the storage part and the gas injection portion of sections above and below the middle section.

* * * * *